(12) United States Patent
Dudley, Jr.

(10) Patent No.: US 9,050,350 B2
(45) Date of Patent: Jun. 9, 2015

(54) METHOD FOR MODULATING OR CONTROLLING CONNEXIN 43(CX43) LEVEL OF A CELL AND REDUCING ARRHYTHMIC RISK

(75) Inventor: Samuel C. Dudley, Jr., Chicago, IL (US)

(73) Assignees: U.S. DEPARTMENT OF VETERANS AFFAIRS, Washington, DC (US); THE BOARD OF TRUSTEES OF THE UNIV. OF ILLINOIS, Urbana, IL (US)

( * ) Notice: Subject to any disclaimer, the term of this patent is extended or adjusted under 35 U.S.C. 154(b) by 0 days.

(21) Appl. No.: 13/507,319

(22) Filed: Jun. 21, 2012

(65) Prior Publication Data
US 2012/0289482 A1 Nov. 15, 2012

Related U.S. Application Data

(63) Continuation-in-part of application No. 12/929,786, filed on Feb. 16, 2011, which is a continuation-in-part of application No. 12/289,005, filed on Oct. 17, 2008, now Pat. No. 8,003,324.

(60) Provisional application No. 61/305,668, filed on Feb. 18, 2010, provisional application No. 60/960,883, filed on Oct. 18, 2007, provisional application No. 61/503,096, filed on Jun. 30, 2011.

(51) Int. Cl.
*A61K 31/675* (2006.01)
*A61K 31/662* (2006.01)

(52) U.S. Cl.
CPC .................................. *A61K 31/662* (2013.01)

(58) Field of Classification Search
CPC .................................................. A61K 31/662
See application file for complete search history.

(56) References Cited

U.S. PATENT DOCUMENTS

| | | |
|---|---|---|
| 5,668,114 A | 9/1997 | Birkmayer |
| 5,849,732 A | 12/1998 | Suzuki et al. |
| 6,339,073 B1 | 1/2002 | Pero |
| 6,833,371 B2 | 12/2004 | Atkinson et al. |
| 7,094,600 B2 | 8/2006 | Wang |
| 7,226,950 B2 | 6/2007 | Choi et al. |
| 8,003,324 B2 | 8/2011 | Dudley, Jr. |
| 2004/0091477 A1 | 5/2004 | Haines et al. |
| 2005/0202093 A1 | 9/2005 | Kohane et al. |
| 2006/0281668 A1 | 12/2006 | Parobok et al. |
| 2007/0212723 A1 | 9/2007 | Dudley et al. |
| 2008/0032940 A1 | 2/2008 | Kalyanaraman et al. |
| 2008/0075666 A1 | 3/2008 | Dudley et al. |
| 2011/0144192 A1 | 6/2011 | Dudley, Jr. |
| 2011/0288044 A1 | 11/2011 | Dudley, Jr. |
| 2012/0288486 A1 | 11/2012 | Dudley, Jr. |
| 2012/0308542 A1 | 12/2012 | Dudley, Jr. |

FOREIGN PATENT DOCUMENTS

| | | |
|---|---|---|
| WO | WO 96/19225 A1 | 6/1996 |
| WO | WO 2007/098065 A1 | 7/2009 |
| WO | WO 2010/129964 A1 | 11/2010 |

OTHER PUBLICATIONS

Sovari et al., Journal of Investigative Medicine, (Apr. 2011) vol. 59, No. 4, pp. 693-694. Abstract No. 6. Meeting Info: 2011 Combined Annual Meeting of the American Federation for Medical Research. Chicago, IL, United States. Apr. 14-15, 2011.*
Iravanian et al., Heart Rhythm 2008, 5(6 Supplement 1): s12-s17.*
Tomaselli et al., Nature Medicine 2010, 16:648-649.*
Liu et al. Biophysical Society Meeting Abstracts 2010, Biophysical Journal, Supplement p. 7a).*
Li et al. Targeting mitochondrial reactive oxygen species as novel therapy for inflammatory diseases and cancers, Journal of Hematology & Oncology 2013, 6:19 (19 pgs).
Smith et al. Mitochondrial pharmacology, Trends in Pharmacological Sciences, Jun. 2012, vol. 33, No. 6, 341-352.
Sovari et al. Mitochondria Oxidative Stress, Connexin43 Remodeling, and Sudden Arrhythmic Death, *Circ Arrhythm Electrophysiol.* 2013;6:623-631.
Final Rejection dated Mar. 11, 2013, in U.S. Appl. No. 12/929,786, filed Feb. 16, 2011.
Office Action dated Sep. 6, 2013, in U.S. Appl. No. 13/551,790, filed Jul. 18, 2012.
Office Action dated Sep. 6, 2013, in U.S. Appl. No. 13/585,396, filed Aug. 14, 2012.
Teo KK, Mitchell LB, Pogue J, Bosch J, Dagenais G, Yusuf S. Effect of ramipril in reducing sudden deaths and nonfatal cardiac arrests in high-risk individuals without heart failure or left ventricular dysfunction. *Circulation.* 2004;110:1413-7.
Kober L, Torp-Pedersen C, Carlsen JE, Bagger H, Eliasen P, Lyngborg K, Videbaek J, Cole DS, Auclert L, Pauly NC. A clinical trial of the angiotensin-converting-enzyme inhibitor trandolapril in patients with left ventricular dysfunction after myocardial infarction. Trandolapril Cardiac Evaluation (TRACE) Study Group. *N Engl J Med.* 1995;333:1670-6.
Xiao HD, Fuchs S, Campbell DJ, Lewis W, Dudley SC, Jr., Kasi VS, Hoit BD, Keshelava G, Zhao H, Capecchi MR, Bernstein KE. Mice with cardiac-restricted angiotensin-converting enzyme (ACE) have atrial enlargement, cardiac arrhythmia, and sudden death. *Am J Pathol.* 2004;165:1019-32.
Sovari AA, Iravanian S, Dolmatova E, Jiao Z, Liu H, Zandieh S, kumar V, Wang K, Bernstein KE, Bonini MG, Duffy HS, Dudley SC. Inhibition of c-Src Tyrosine Kinase Prevents Angiotensin II-Mediated Connexin-43 Remodeling and Sudden Cardiac Death. *JACC.* 2011;58:2332-9.
Kasi VS, Xiao HD, Shang LL, Iravanian S, Langberg J, Witham EA, Jiao Z, Gallego CJ, Bernstein KE, Dudley SC, Jr. Cardiac-restricted angiotensin-converting enzyme overexpression causes conduction defects and connexin dysregulation. *Am J Physiol Heart Circ Physiol.* 2007;293:H182-H192, with supplement (1 pg).

(Continued)

*Primary Examiner* — Doug Schultz
(74) *Attorney, Agent, or Firm* — Dinesh Agarwal, P.C.

(57) ABSTRACT

A method of modulating or controlling connexin 43 (Cx43) level of a cell includes inducing mitochondrial reactive oxygen species (ROS) production in the cell.

13 Claims, 8 Drawing Sheets
(5 of 8 Drawing Sheet(s) Filed in Color)

(56) References Cited

OTHER PUBLICATIONS

Iravanian S, Sovari AA, Lardin HA, Liu H, Xiao HD, Dolmatova E, Jiao Z, Harris BS, Witham EA, Gourdie RG, Duffy HS, Bernstein KE, Dudley SC, Jr. Inhibition of renin-angiotensin system (RAS) reduces ventricular tachycardia risk by altering connexin43. *J Mol Med (Berl)*. 2011.89:677-87.

Morita N, Sovari AA, Xie Y, Fishbein MC, Mandel WJ, Garfinkel A, Lin SF, Chen PS, Xie LH, Chen F, Qu Z, Weiss JN, Karagueuzian HS. Increased susceptibility of aged hearts to ventricular fibrillation during oxidative stress. *Am J Physiol Heart Circ Physiol*. 2009;297:H1594-H1605, with supplement (3 pgs).

Sato D, Xie LH, Sovari AA, Tran DX, Morita N, Xie F, Karagueuzian H, Garfinkel A, Weiss JN, Qu Z. Synchronization of chaotic early afterdepolarizations in the genesis of cardiac arrhythmias. *Proc Natl Acad Sci U S A*. 2009;106:2983-8, with supplement (17 pgs).

Brown DA, O'Rourke B. Cardiac mitochondria and arrhythmias. *Cardiovasc Res*. 2010;88:241-9.

Jeong EM, Liu M, Sturdy M, Gao G, Varghese ST, Sovari AA, Dudley SC. Metabolic stress, reactive oxygen species, and arrhythmia. *J Mol Cell Cardiol*. 2012;52:454-63.

Sovari AA, Bonini MG, Dudley SC. Effective antioxidant therapy for the management of arrhythmia. *Expert Rev Cardiovasc Ther*. 2011;9:797-800.

Whaley-Connell A, Govindarajan G, Habibi J, Hayden MR, Cooper SA, Wei Y, Ma L, Qazi M, Link D, Karuparthi PR, Stump C, Ferrario C, Sowers Jr. Angiotensin II-mediated oxidative stress promotes myocardial tissue remodeling in the transgenic (mRen2) 27 Ren2 rat. *Am J Physiol Endocrinol Metab*. 2007;293:E355-E363.

Sesso HD, Buring JE, Christen WG, Kurth T, Belanger C, MacFadyen J, Bubes V, Manson JE, Glynn RJ, Gaziano JM. Vitamins E and C in the prevention of cardiovascular disease in men: the Physicians' Health Study II randomized controlled trial. *J Am Med Assoc*. 2008;300:2123-33.

Santos CX, Anilkumar N, Zhang M, Brewer AC, Shah AM. Redox signaling in cardiac myocytes. *Free Radic Biol Med*. 2011;50:777-93.

Stefanska J, Pawliczak R. Apocynin: molecular aptitudes. *Mediators Inflamm*. 2008;2008:106507, with supplement (10 pgs).

de Mendez I, Garrett MC, Adams AG, Leto TL. Role of p67-phox SH3 domains in assembly of the NADPH oxidase system. *J Biol Chem*. 1994;269:16326-32.

Rees DD, Palmer RM, Schulz R, Hodson HF, Moncada S. Characterization of three inhibitors of endothelial nitric oxide synthase in vitro and in vivo. *Br J Pharmacol*. 1990;101:746-52 (7 pgs).

Shen RS, Alam A, Zhang YX. Inhibition of GTP cyclohydrolase I by pterins. *Biochim Biophys Acta*. 1988;965:9-15.

Pacher P, Nivorozhkin A, Szabo C. Therapeutic effects of xanthine oxidase inhibitors: renaissance half a century after the discovery of allopurinol. *Pharmacol Rev*. 2006;58:87-114.

Krishna MC, Grahame DA, Samuni A, Mitchell JB, Russo A. Oxoammonium cation intermediate in the nitroxide-catalyzed dismutation of superoxide. *Proc Natl Acad Sci U S A*. 1992;89:5537-41.

Murphy MP, Smith RA. Targeting antioxidants to mitochondria by conjugation to lipophilic cations. *Annu Rev Pharmacol Toxicol*. 2007;47:629-56, with supplement (2 pgs).

Liu M, Liu H, Dudley SC, Jr. Reactive oxygen species originating from mitochondria regulate the cardiac sodium channel. *Circ Res*. 2010;107:967-74, with supplement (5 pgs).

Morita N, Lee Jh, Xie Y, Sovari A, Qu Z, Weiss JN, Karagueuzian HS. Suppression of re-entrant and multifocal ventricular fibrillation by the late sodium current blocker ranolazine. *JACC*. 2011;57:366-75.

el-Fouly MH, Trosko JE, Chang CC. Scrape-loading and dye transfer. A rapid and simple technique to study gap junctional intercellular communication. *Exp Cell Res*. 1987;168:422-30.

Van Norstrand DW, Asimaki A, Rubinos C, Dolmatova E, Srinivas M, Tester DJ, Saffitz JE, Duffy HS, Ackerman MJ. Connexin43 mutation causes heterogeneous gap junction loss and sudden infant death. *Circulation*. 2011;125:474-81.

Roig E, Perez-Villa F, Morales M, Jimenez W, Orus J, Heras M, Sanz G. Clinical implications of increased plasma angiotensin II despite ACE inhibitor therapy in patients with congestive heart failure. *Eur Heart J*. 2000;21:53-7.

Gutstein DE, Morley GE, Tamaddon H, Vaidya D, Schneider MD, Chen J, Chien KR, Stuhlmann H, Fishman GI. Conduction slowing and sudden arrhythmic death in mice with cardiac-restricted inactivation of connexin43. *Circ Res*. 2001;88:333-9.

Reaume AG, de Sousa PA, Kulkarni S, Langille BL, Zhu D, Davies TC, Juneja SC, Kidder GM, Rossant J. Cardiac malformation in neonatal mice lacking connexin43. *Science*. 1995;267:1831-4.

Haendeler J, Hoffmann J, Brandes RP, Zeiher AM, Dimmeler S. Hydrogen peroxide triggers nuclear export of telomerase reverse transcriptase via Src kinase family-dependent phosphorylation of tyrosine 707. *Mol Cell Biol*. 2003;23:4598-610.

Aikawa R, Komuro I, Yamazaki T, Zou Y, Kudoh S, Tanaka M, Shiojima I, Hiroi Y, Yazaki Y. Oxidative stress activates extracellular signal-regulated kinases through Src and Ras in cultured cardiac myocytes of neonatal rats. *J Clin Invest*. 1997;100:1813-21.

Abadir PM, Foster DB, Crow M, Cooke CA, Rucker JJ, Jain A, Smith BJ, Burks TN, Cohn RD, Fedarko NS, Carey RM, O'Rourke B, Walston JD. Identification and characterization of a functional mitochondrial angiotensin system. *Proc Natl Acad Sci U S A*. 2011;108:14849-54, with supp (4 pgs).

Ago T, Kuroda J, Pain J, Fu C, Li H, Sadoshima J. Upregulation of Nox4 by hypertrophic stimuli promotes apoptosis and mitochondrial dysfunction in cardiac myocytes. *Circ Res*. 2010;106:1253-64, with supplement (24 pgs).

Kuroda J, Ago T, Matsushima S, Zhai P, Schneider MD, Sadoshima J. NADPH oxidase 4 (Nox4) is a major source of oxidative stress in the failing heart. *Proc Natl Acad Sci U S A*. 2010;107:15565-70, with supplement (8 pgs).

Bendall JK, Cave AC, Heymes C, Gall N, Shah AM. Pivotal role of a gp91(phox)-containing NADPH oxidase in angiotensin II-induced cardiac hypertrophy in mice. *Circulation*. 2002;105:293-6.

Doughan AK, Harrison DG, Dikalov SI. Molecular mechanisms of angiotensin II-mediated mitochondrial dysfunction: linking mitochondrial oxidative damage and vascular endothelial dysfunction. *Circ Res*. 2008;102:488-96, with supplement (24 pgs).

Bedard K, Krause KH. The NOX family of ROS-generating NADPH oxidases: physiology and pathophysiology. *Physiol Rev*. 2007;87:245-313.

Dikalov S. Cross talk between mitochondria and NADPH oxidases. *Free Radic Biol Med*. 2011;51:1289-301.

Zorov DB, Juhaszova M, Sollott SJ. Mitochondrial ROS-induced ROS release: an update and review. *Biochim Biophys Acta*. 2006;1757:509-17.

Beresewicz A, Horackova M. Alterations in electrical and contractile behavior of isolated cardiomyocytes by hydrogen peroxide: possible ionic mechanisms. *J Mol Cell Cardiol*. 1991;23:899-918.

Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res*. 2010;107:106-16, with supplement (24 pgs).

Dai DF, Johnson SC, Villarin JJ, Chin MT, Nieves-Cintron M, Chen T, Marcinek DJ, Dorn GW, Kang YJ, Prolla TA, Santana LF, Rabinovitch PS. Mitochondrial oxidative stress mediates angiotensin II-induced cardiac hypertrophy and Gαq overexpression-induced heart failure. *Circ Res*. 2011;108:837-46, with supplement (50 pgs).

van de Wal RM, Plokker HW, Lok DJ, Boomsma F, van der Horst FA, van Veldhuisen DJ, van Gilst WH, Voors AA. Determinants of increased angiotensin II levels in severe chronic heart failure patients despite ACE inhibition. *Int J Cardiol*. 2006;106:367-72.

Canton M, Menazza S, Sheeran FL, Polverino de LP, Di LF, Pepe S. Oxidation of myofibrillar proteins in human heart failure. *JACC*. 2011;57:300-9.

Banfi C, Brioschi M, Barcella S, Veglia F, Biglioli P, Tremoli E, Agostoni P. Oxidized proteins in plasma of patients with heart failure: role in endothelial damage. *Eur J Heart Fail*. 2008;10:244-51.

Bruce AF, Rothery S, Dupont E, Severs NJ. Gap junction remodelling in human heart failure is associated with increased interaction of connexin43 with ZO-1. *Cardiovasc Res*. 2008;77:757-65, with supplement (7 pgs).

(56) References Cited

OTHER PUBLICATIONS

Kaprielian RR, Gunning M, Dupont E, Sheppard MN, Rothery SM, Underwood R, Pennell DJ, Fox K, Pepper J, Poole-Wilson PA, Severs NJ. Downregulation of immunodetectable connexin43 and decreased gap junction size in the pathogenesis of chronic hibernation in the human left ventricle. *Circulation*. 1998;97:651-60.

Baines CP. How and when do myocytes die during ischemia and reperfusion: the late phase. *J Cardiovasc Pharmacol Ther*. 2011;16:239-43.

Kieken F, Mutsaers N, Dolmatova E, Virgil K, Wit AL, Kellezi A, Hirst-Jensen BJ, Duffy HS, Sorgen PL. Structural and molecular mechanisms of gap junction remodeling in epicardial border zone myocytes following myocardial infarction. *Circ Res*. 2009;104:1103-12, with supplement (18 pgs).

Borgstahl et al., The Structure of Human Mitochondrial Manganese Superoxide Dismutase Reveals a Novel Tetrameric Interface of Two 4-Helix Bundles. Cell 71;107-118, Oct. 1992.

McCord & Fridovch, Superoxide Dismutase, An Enzymic Function for Erythrocuprein (Hemocuprein) Journal of Biological Chemistry, 244: 6049-6055, 1969.

Liochev and Fridovich, The effects of superoxide dismutase on H2O2 formation. Free Radical Biology & Medicine 42 (2007) 1465-1469.

Sovari AA, Rutledge CA, Jeong E-M, Dolmatova E, Arasu D, Liu H, Vandani N, Gu L, Zandieh S, Xiao L, Bonini MG, Duffy HS, Dudley SC. Mitochondria-Targeted Antioxidant Therapy Prevents Connexin 43 Remodeling and Sudden Death Caused by Renin-Angiotensin System Activation. Circulation. 2012; 126: A19711 (3 pages).

Sovari AA, Jeong EM, Zandieh S, Gu L, Iravanian S, Bonini M, Dudley SC. Mitochondria-Targeted Antioxidant Therapy Prevents Angiotensin II Medicated Connexin 43 Remodeling and Sudden Arrhythmic Death. Circulation, vol. 124, (21 Meeting Abs.) Supp. 1, Nov. 22, 2011. Abstract 15801 (1 pg).

Brugada P, Brugada J. Right bundle branch block, persistent ST segment elevation and sudden cardiac death: a distinct clinical and electrocardiographicsyndrome. A multicenter report. *J Am Coll Cardiol*. 1992;20:1391-1396.

Kadish, A. et al. 2006. Patients with recently diagnosed nonischemic cardiomyopathy benefit from implantable cardioverter-defbrillators. *J. Am Coll. Cardiol*. 47:2477-2482.

Amin AS, Verkerk AO, Bhuiyan ZA, Wilde AAM, Tan HL. Novel Brugada syndrom-causing mutation in ion-conducting pore of cardiac Na_ channel does not affect ion selectivity properties. *Acta Physiol Scand*. 2005;185:291-301.

Baroudi G, Napolitano C, Priori SG, Del Bufalo A, Chahine M. Loss of function associated with novel mutations of the SCN5A gene in patients with Brugada syndrome. *Can J Cardiol*. 2004;20:425-430.

Baroudi G, Acharfi S, Larouche C, Chahine M. Expression and Intracellular localization of an SCN5A double mutant R1232W/T1620M implicated in Brugada syndrome. *Circ Res*. 2002;90:e11-e16.

Baroudi G, Pouliot V, Denjoy I, Guicheney P, Shrier A, Chahine M. Novel mechanism for Brugada syndrome: Defective surface localization of an SCN5A mutant (R1432G). *Circ Res*. 2001;88:e78-e83.

Vatta M, Dumaine R, Antzelevitch C, Brugada R, Li H, Bowles NE, Nademanee K, Brugada J, Brugada P, Towbin JA. Novel mutations in domain I of SCN5A cause Brugada syndrome. *Mol Genet Metab*. 2002;75:317-324.

London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC Jr. Mutation in glycerol-3-phosphate dehydrogenase 1-like gene (GPD1-L) decreases cardiac Na_ current and causes inherited arrhythmias. *Circulation*. 2007;116:2260-2268.

Van Norstrand DW, Valdivia CR, Tester DJ, Ueda K, London B, Makielski JC, Ackerman MJ. Molecular and functional characterization of novel glycerol-3-phosphate dehydrogenase 1 like gene (GPD1-L) mutations in sudden infant death syndrome. *Circulation*. 2007;116:2253-2259.

Shen, W. et al. 2006. Involvement of glycerol-3-phosphate dehydrogenase in modulating the NADH/NAD+ ratio provides evidence of a mitochondrial glycerol-3-phosphate shuttle in *Arabidopis*. *Plant Cell*. 18:422-441.

Papadatos GA, Wallerstein PMR, Head CEG, Ratcliff R, Brady PA, Benndorf K, Saumarez RC, Trezise AEO, Huang CLH, Vandenberg JI, Colledge WH, Grace AA. Slowed conduction and ventricular tachycardia after targeted disruption of the cardiac sodium channel gene SCN5a. *Proc Natl Acad Sci U S A*. 2002;99:6210-6215.

Knollmann BC, Schober T, Petersen AO, Sirenko SG, Franz MR. Action potential characterization in intact mouse heart: steady-state cycle length dependence and electrical restitution. *Am J Physiol Heart Circ Physiol*. 2007;292:H614-H621.

Killeen MJ, Thomas G, Gurugn IS, Goddard CA, Fraser JA, Mahaut-Smith MP, Colledge WH, Grace AA, Huang CLH. Arrhythmogenic mechanisms in the isolated perfused hypokalaemic murine heart. *Acta Physiol*. 2007;189:33-46.

Zalba, G. et al. 2000. Vascular NADH/NADPH oxidase is involved in enhanced superoxide production in spontaneously hypertensive rats. *Hypertension*. 35:1055-1061.

Javesghani, D. et al. 2002. Molecular characterization of a superoxide-generating NAD(P)H oxidase in the ventilator muscles. *Am. J. Respir. Crit. Care Med*. 165: 412-418.

Zicha, S. Maltsev, V.A., Nattel, S., Sabbah, H.N. and Undrovinas, A.L. 2004. Posttranscriptional alterations in the expression of cardiac Na+ channel subunits in chronic heart failure. *J. Mol. Cell. Cardiol*. 37: 91-100.

Schreibmayer W, Dascal N, Lotan I, Wallner M, Weigl L. Molecular mechanism of protein kinase C modulation of sodium channel_-subunits expressed in *Xenopus* oocytes. *FEBS Lett*. 1991;291:341-344.

Ward, C.A., and Giles, W.R. 1997. Ionic mechanism of the effects of hydrogen peroxide in rat ventricular myocytes. *J. Physiol*. 500: 631-642.

Takeishi, Y., Jalili, T., Ball, N.A. and Walsh, R.A. 1999. Responses of cardiac protein kinase C isoforms to distinct pathological stimuli are differently regulated. *Circ. Res*. 85:264-271.

Sharma, A. and Singh, M. 2001. Protein kinase C activation and cardioprotective effect of preconditioning with oxidative stress in isolated rat heart. *Mol. Cell. Biochem*. 219: 1-6.

Brawn, M.K., Chiou, W.J. and Leach, K.L. 1995. Oxidant-induced activation of protein kinase C in UC11Mg cells. *Free Radic. Res*. 22: 23-37.

Pfahnl AE, Viswanathan PC, Weiss R, Shang LL, Sanyal S, Shusterman V, Kornblit C, London B, Dudley SC Jr. A sodium channel pore mutation causing Brugada syndrome. *Heart Rhythm*. 2007;4:46-53.

Kyndt, F. et al. 2001. Novel SCN5A mutation leading either to isolated cardiac conduction defect or Brugada syndrome in a large French family. *Circulation*. 104:3081-3086.

Tipparaju SM, Saxena N, Liu SQ, Kumar R, Bhatnagar A. Differential regulation of voltage-gated K_ channels by oxidized and reduced pyridine nucleotide coenzymes. *Am J Physiol Cell Physiol*. 2005;288: C366-C376.

Tipparaju SM, Liu SQ, Barski OA, Bhatnagar A. NADPH binding to _-subunit regulates inactivation of voltage-gated K_ channels. *Biochem Biophys Res Commun*. 2007;359:269-276.

Heiner I, Eisfeld J, Halaszovich CR, Wehage E, JuÖngling E, Zitt C LuÖckhoff A. Expression profile of the transient receptor potential (TRP) family in neutrophil granulocytes: evidence for currents through long TRP channel 2 induced by ADP-ribose and NAD. *Biochem J*. 2003;371: 1045-1053.

Herson PS, Dulock KA, Ashford ML. Characterization of a nicotinamideadenine dinucleotide-dependent cation channel in the CRI-G1 rat insulinoma cell line. *J Physiol*. 1997;505:65-76.

Alvarez J, Camaleno J, Garcia-Sancho J, Herreros B. Modulation of Ca2_-dependent K_ transport by modifications of the NAD_/NADH ratio in intact human red cells. *Biochim Biophys Acta*. 1986;856: 408-411.

Zima AV, Copello JA, Blatter LA. Effects of cytosolic NADH/NAD_ levels on sarcoplasmic reticulum Ca2_ release in permeabilized rat ventricular myocytes. *J Physiol*. 2004;555:727-741.

(56) References Cited

OTHER PUBLICATIONS

Park MK, Lee SH, Ho WK, Earm YE. Redox agents as a link between hypoxia and the responses of ionic channels in rabbit pulmonary vascular smooth muscle. *Exp Physiol.* 1995;80:835-842.

Aon MA, Cortassa S, Marban E, O'Rourke B. Synchronized whole cell oscillations in mitochondrial metabolism triggered by a local release of reactive oxygen species in cardiac myocytes. *J Biol Chem.* 2003;278: 44735-44744.

Di LF, Menabo R, Canton M, Barile M, Bernardi P. Opening of the mitochondrial permeability transition pore causes depletion of mitochondrial and cytosolic NAD_ and is a causative event in the death of myocytes in postischemic reperfusion of the heart. *J Biol Chem.* 2001; 276:2571-2575.

Choudhary G, Dudley SC Jr. Heart failure, oxidative stress, and ion channel modulation. *Congest Heart Fail.* 2002;8:148-155.

Pillai JB, Isbatan A, Imai Si, Gupta MP. Poly(ADP-ribose) polymerase-1-dependent cardiac myocyte cell death during heart failure is mediated by NAD_ depletion and reduced Sir2_ deacetylase activity. *J Biol Chem.* 2005;280:43121-43130.

Dzhanashiya PK, Vladytskaya OV, Salibegashvili NV. Efficiency and mechanisms of the antioxidant effect of standard therapy and refracterin in the treatment of chronic heart failure in elderly patients with postinfarction cardiosclerosis. *Bull Exp Biol Med.* 2004;138:412-414.

Shang LL, Pfahnl AE, Sanyal S, Jiao Z, Allen J, Banach K, Fahrenbach J, Weiss D, Taylor WR, Zafari AM, Dudley SC Jr. Human heart failure is associated with abnormal C-terminal splicing variants in the cardiac sodium channel. *Circ Res.* 2007;101:1146-1154, and Online Supplement (pp. 1-10).

Makielski JC, Farley A. Na_ current in human ventricle: implications for sodium loading and homeostasis. *J Cardiovasc Electrophysiol.* 2006;17: S15-S20.

Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol.* 2005;38:475-483.

Ajiro Y, Hagiwara N, Kasanuki H. Assessment of markers for idendifying patients at risk for life-threatening arrhythmic events in Brugada syndrome. *J Cardiovasc Electrophysiol.* 2005;16:45-51.

Gellens et al. Primary Structure and Functional Expression of the Human Cardiac Tetrodotoxin-Insensitive Voltage-Dependent Sodium-Channel. *Proceedings of the National Academy of Sciences of the United States of America* 89, 554-558 (1992).

Wang et al. Genomic organization of the human SCN5A gene encoding the cardiac sodium channel. *Genomics* 34, 9-16 (1996).

George et al. Assignment of the human heart tetrodotoxin-resistant voltage-gated Sodium channel alpha-subunit gene (SCN5A) to band 3p21. *Cytogenet. Cell Genet.* 68, 67-70 (1995).

Schott et al. Cardiac conduction defects associate with mutations in SCN5A. *Nat. Genet.* 23, 20-21 (1999).

Tan et al. A calcium sensor in the sodium channel modulates cardiac excitability. *Nature* 415, 442-447 (2002).

Zubay, Biochemistry, Chapter 10, part II Carbohydrate metabolism and chemical energy, p. 400-403 (1984).

Remington's Pharmaceutical Sciences, Mace Publishing Company, Philadelphia, Pa., 17th ed. (1985).

Alings, M. and Wilde A. "Brugada" Syndrome: Clinical Data and Suggested Pathophysiological Mechanism. *Circulation* 1999; 99:666-673.

Brugada J, Brugada R, Antzelevitch C et al. Long-term follow-up of individuals with the electrocardiographic pattern of right bundle-branch block and ST-segment elevation in precordial leads V1 to V3. *Circulation.* 2002;105:73-78.

Zhou, M. Diwu Z., Panchuk-Voloshina, N. and Haugland. A Stable Nonfluorescent Derivative of Resorufin for the Fluorometric Determination of Trace Hydrogen Peroxide: Applications in Detecting the Activity of Phagocyte NADPH Oxidase and Other Oxidases. *Analytical Biochemistry* 253 (1997) 162-168.

Mohanty, J.G., Jaffe, J.S., Schulman, E.S. and Raible, D.G . . . A Highly Sensitive Fluorescent Micro-Assay of H2O Release from Activated Human Leukocytes Using a Dihydroxyphenoxazine Derivative. *Journal of Immunological Methods* 202 (1997) 133-141.

Liu M, Sanyal S, Gao G, Gurung IS, Zhu X, Gaconnet G, Kerchner LJ, Shang LL, Huang CLH, Grace A, London B, Dudley SC, Jr. Cardiac $Na^+$ current regulation by pyridine nucleotides. *Circ Res.* 2009; 105:737-45, Supplemental Material (pp. 1-8), and Author manuscript Cir Res Oct. 2009; 105(8):737-745.

Shaw RM, Rudy Y. Ionic mechanisms of propagation in cardiac tissue: roles of the sodium and L-type calcium currents during reduced excitability and decreased gap junction coupling. *Circ Res.* 1997; 81:727-41.

Shimizu W, Aiba T, Kamakura S. Mechanisms of disease: current understanding and future challenges in Brugada syndrome. *Nat Clin Pract Cardiovasc Med.* 2005; 2:408-14.

Andrukhiv A, Costa ADT, West I, Garlid KD. Opening of $mitoK_{ATP}$ increases superoxide generation from complex I of the electron transport chain. *Am J Physiol Heart Circ Physiol.* 2006; 291:H2067-H2074.

Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

Mallat Z, Philip I, Lebret M, Chatel D, Maclouf J, Tedgui A. Elevated levels of 8-iso-prostaglandin F2a in pericardial fluid of patients with heart failure : a potential role for in vivo oxidant stress in ventricular dilatation and progression to heart failure. *Circulation.* 1998: 97:1536-9.

Hill MF, Singal PK. Right and left myocardial antioxidant responses during heart failure subsequent to myocardial infarction. *Circulation.* 1997; 96:2414-20 (11 pages).

Dhalla AK, Singal PK. Antioxidant changes in hypertrophied and failing guinea pig hearts. *Am J Physiol Heart Circ Physiol.* 1994; 266:H1280-H1285.

Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

Zorov DB, Filburn CR, Klotz LO, Zweier JL, Sollott SJ. Reactive oxygen species (ROS)-induced ROS release: a new phenomenon accompanying induction of the mitochondrial permeability transition in cardiac myocytes. *J Exp Med.* 2000; 192:1001-14.

Costa ADT, Pierre SV, Cohen MV, Downey JM, Garlid KD. cGMP signalling in pre- and post-conditioning: the role of mitochondria. *Cardiovasc Res.* 2008; 77:344-52.

Ogbi M, Chew CS, Pohl J, Stuchlik O, Ogbi S, Johnson JA. Cytochrome c oxidase subunit IV as a marker of protein kinase Ce function in neonatal cardiac myocytes: implications for cytochrome c oxidase activity. *Biochem J.* 2004; 382:923-32.

Clarke SJ, McStay GP, Halestrap AP. Sanglifehrin A Acts as a Potent Inhibitor of the Mitochondrial Permeability Transition and Reperfusion Injury of the Heart by Binding to Cyclophilin-D at a Different Site from Cyclosporin A. *J Biol Chem* 2002;277:34793-9.

Sato T, O'Rourke B, Marban E. Modulation of mitochondrial ATP-dependent $K^+$ channels by protein kinase C. *Circ Res.* 1998; 83:110-4.

O'Rourke B. Evidence for mitochondrial $K^+$ channels and their role in cardioprotection. *Circ Res.* 2004; 94:420-32, and Supplement (pp. 1-6).

Chen Q, Vazquez E, Moghaddas S, Hoppel C, Lesnefsky E. Production of reactive oxygen species by mitochondria. *J Biol Chem.* 2003; 278:36027-31.

Akar FG, Aon MA, Tomaselli GF, O'Rourke B. The mitochondrial origin of postischemic arrhythmias. *J Clin Invest.* 2005; 115:3527-35.

Murphy MP. How mitochondria produce reactive oxygen species. *Biochem J.* 2009; 417:1-13.

O'Rourke B, Ramza B, Marban E. Oscillations of membrane current and excitability driven by metabolic oscillations in heart cells. *Science.* 1994; 265:962-6.

Murray KT, Hu N, Daw JR, Shin HG, Watson MT, Mashburn AB, George AL Jr. Functional effects of protein kinase C activation on the human cardiac Na_ channel. *Circ Res.* 1997;80:370-376.

(56) References Cited

OTHER PUBLICATIONS

Zhou J, Yi J, Hu N, George AL Jr, Murray KT. Activation of protein kinase A modulates trafficking of the human cardiac sodium channel in Xenopus oocytes. *Circ Res*. 2000;87:33-38.

Hallaq et al. Quantitation of protein kinase A-mediated trafficking of cardiac sodium channels in living cells. *Cardiovascular Research* 72 (2006) 250-261.

Zhou J, Shin HG, Yi J, Shen W, Williams CP, Murray KT. Phosphorylation and putative ER retention signals are required for protein kinase A-mediated potentiation of cardiac sodium current. *Circ Res*. 2002;91: 540-546.

Zhang F, Jin S, Yi F, Xia M, Dewey WL, Li PL. Local production of O2 by NAD(P)H oxidase in the sarcoplasmic reticulum of coronary arterial myocytes: cADPR-mediated Ca2_ regulation. *Cell Signal*. 2008;20: 637-644.

Nitti et al. PKC signaling in oxidative hepatic damage. Molecular Aspects of Medicine 29 (2008) 36-42.

Bruzzone et al. Extracellular NAD+ regulates intracellular calcium levels and induces activation of human granulocytes. Biochem. J. (2006) 393, 697-704.

Romanello et al. Extracellular NAD1 Induces Calcium Signaling and Apoptosis in Human Osteoblastic Cells. Biochemical and Biophysical Research Communications 285, 1226-1231 (2001).

Budas & Mochly-Rosen. Mitochondrial protein kinase Cε(PKCε): emerging role in cardiac.protection from ischaemic damage. Biochemical Society Transactions (2007) vol. 35, part 5, 1052-1054.

Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SCJr. Uncoupled cardiac nitric oxide synthase mediates diastolic dysfunction. *Circulation*. 2010; 121:519-28, and Supp. Data (21 pp.).

Sorescu D, Weiss D, Lassegue B, Clempus RE, Szocs K, Sorescu GP, Valppu L, Quinn MT, Lambeth JD, Vega JD, Taylor WR, Griendling KK. Superoxide production and expression of Nox family proteins in human atherosclerosis. *Circulation*. 2002; 105:1429-35.

Pacher P, Nivorozhkin A, Szabo C. Therapeutic effects of xanthine oxidase inhibitors: Renaissance half a century after the discovery of allopurinol. *Pharmacol Rev*. 2006; 58:87-114.

Kobayashi K, Neely JR. Control of maximum rates of glycolysis in rat cardiac muscle. *Circ Res*. 1979; 44:166-75.

Li Q, Hwang YC, Ananthakrishnan R, Oates PJ, Guberski D, Ramasamy R. Polyol pathway and modulation of ischemia-reperfusion injury in Type 2 diabetic BBZ rat hearts. *Cardiovasc Diabetol*. 2008; 7:33-44 (11 pages).

Moir AM, Zammit VA. Insulin-independent and extremely rapid switch in the partitioning of hepatic fatty acids from oxidation to esterification in starved-refed diabetic rats. *Biochem J*. 1995; 305:953-8.

van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE*. 2008; 3:e2013 (12 pages).

Liang HL, Arsenault J, Mortensen J, Park F, Johnson CP, Nilakanta V. Partial attenuation of cytotoxicity and apoptosis by SOD1 in ischemic renal epithelial cells. *Apoptosis*. 2009; 14:1176-89.

Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res*. 2010; 107:106-16, and Online Supp. (12 pages).

Murphy E, Steenbergen C. Preconditioning: the mitochondrial connection. *Annu Rev Physiol*. 2007; 69:51-67.

Barth E, Stämmler G, Speiser B, Schaper J. Ultrastructural quantitation of mitochondria and myofilaments in cardiac muscle from 10 different animal species including man. *J Mol Cell Cardiol*. 1992; 24:669-81.

Boveris A, Oshino N, Chance B. The cellular production of hydrogen peroxide. *Biochem J*. 1972; 128:617-630.

Batandier C, Fontaine E, Keriel C, Leverve X. Determination of mitochondrial and reactive oxygen species: methodological aspects. *J Cell Mol Med*. 2002; 6:175-87.

Panov A, Schonfeld P, Dikalov S, Hemendinger R, Bonkovsky HL, Brooks BR. The Neuromediator glutamate, through specific substrate interactions, enhances mitochondrial ATP production and reactive oxygen species generation in monsynaptic brain mitochondria. *J Biol Chem*. 2009; 284:14448-56.

Han D, Antunes F, Canali R, Rettori D, Cadenas E. Voltage-dependent anion channels control the release of the superoxide anion from mitochondria to cytosol. *J Biol Chem*. 2003; 278:5557-63.

Brown D, Aon MA, Akar FG, Liu T, Sorarrain N, O'Rourke B. Effects of 4'-chlorodiazepam on cellular excitation-constraction coupling and ischaemia-reperfusion injury in rabbit heart. *Cardiovasc Res*. 2008; 79:141-9.

Valdivia CR, Ueda K, Ackerman MJ, Makielski JC. GPD1L links redox state to cardiac excitability by PKC-dependent phosphorylation of the sodium channel SCN5A. *AJP—Heart and Circulatory Physiology*. 2009; 297:H1446-H1452.

Zelent B, Troxler T, Vanderkooi JM. Temperature dependence for fluorescence of β-NADH in glycerol/water solution and in trehalose/sucrose glass. *Journal of Fluorescence*. 2007; 17:37-42.

Liu M, Gaconnet G, London B, Dudley, Jr. S.C. A Central Role of Mitochondria in the Regulation of Sodium Current. Presentation at the Cardiac Electrophysiology Society, Orlando, Florida (Nov. 14, 2009) (1 page).

Yang H, Yang T, Baur JA, Perez E, Matsui T, Carmona JJ, Lamming D, Souza-Pinto NC, Bohr VA, Rosenzweig A, de Cabo R, Sauve A, Sinclair DA. Nutrient-sensitive mitochondrial NAD_ levels dictate cell survival. *Cell*. 2007;130:1095-1107.

Lin SJ, Guarente L. Nicotinamide adenine dinucleotide, a metabolic regulator of transcription, longevity and disease. *Curr Opin Cell Biol*. 2003;15:241-246.

Herbert JM, Augereau JM, Gleye J, Maffrand JP. Chelerythrine is a potent and specific inhibitor of protein kinase C. *Biochem Biophys ResCommun*. 1990;172:993-999.

Chao MD, Chen IS, Cheng JT. Inhibition of protein kinase C translocation from cytosol to membrane by chelerythrine. *Planta Med*. 1998;64: 662-663.

Frohnwieser B, Chen L, Schreibmayer W, Kallen R. Modulation of the human cardiac sodium channel alpha-subunit by cAMP-dependent protein kinase and the responsible sequence domain. *J Physiol (London)*. 1997;498:309-318.

Glass DB, Lundquist LJ, Katz BM, Walsh DA. Protein kinase inhibitor-(6-22)-amide peptide analogs with standard and nonstandard amino acid substitutions for phenylalanine 10. Inhibition of cAMP-dependent protein kinase. *J Biol Chem*. 1989;264:14579-14584.

Shin HG, Murray KT. Conventional protein kinase C isoforms and cross-activation of protein kinase A regulate cardiac Na_ current. *FEBS Lett*. 2001;495:154-158.

Biswas S, DiSilvestre D, Tian Y, Halperin VL, Tomaselli GF. Calciummediated dual-mode regulation of cardiac sodium channel gating. *Circ Res*. 2009;104:870-878, and Supp. Material (10 pages).

Casini S, Verkerk AO, van Borren MM, van Ginneken AC, Veldkamp MW, de Bakker JM, Tan HL. Intracellular calcium modulation of voltage-gated sodium channels in ventricular myocytes. *Cardiovasc Res*. 2009;81:72-81.

Brisson D, Vohl M, St Pierre J, Hudson T, Gaudet D. Glycerol: a neglected variable in metabolic process? *Bioessays*. 2001;23.6:534-542.

Antzelevitch C, Brugada P, Borggrefe M, et al. Brugada syndrome: report of the second consensus conference: endorsed by the Heart Rhythm Society and the European Heart Rhythm Association. *Circulation*. 2005; 111 :659-670.

Brugada J, Brugada P. Further characterization of the syndrome of right bundle branch block, ST segment elevation, and sudden cardiac death. *J Cardiovasc Electrophysiol*. 1997; 8:325-331.

Grant AD. Electrophysiological basis and genetics of Brugada syndrome. *J Cardiovasc Electrophysiol*. 2005; 16:S3-7.

Chen Q, Kirsch GE, Zhang 0, et al. Genetic basis and molecular mechanism for idiopathic ventricular fibrillation. *Nature*. 1998; 392:293-296.

Priori SG, Napolitano C, Gasparini M, et al. Clinical and genetic heterogeneity of right bundle branch block and ST-segment elevation syndrome: A prospective evaluation of 52 families. *Circulation*. 2000; 102:2509-2515.

(56) References Cited

OTHER PUBLICATIONS

Valdivia CR, Tester OJ, Rok BA, et al. A trafficking defective, Brugada syndromecausing SCN5A mutation rescued by drugs. *Cardiovasc Res*. 2004; 62:53-62.

Brugada R, Brugada J, Antzeievitch G, et al. Sodium channel blockers identify risk for sudden death in patients with ST-segment elevation and right bundle branch block but structurally normal hearts. *Circulation*. 2000; 101:510-515.

Pollevick GO, Schimpf R, Aizawa Y, et al. Loss of function in calcium channel activity secondary to a mutation in CACNB2b modulates the clinical manifestation of a combined Brugada syndrome-hort aT phenotype. *Circulation*. 2006; 114:11-193 (Abstract—3 pages).

Yan GX, Antzelevitch C. Cellular basis for the Brugada syndrome and other mechanisms of arrhythmogenesis associated with ST-segment elevation. *Circulation*. 1999; 100:1660-1666.

Weiss R, Barmada MM, Nguyen T, et al. Clinical and molecular heterogeneity in the Brugada syndrome: a novel gene locus on chromosome 3. *Circulation*. 2002;105:707-713.

Walz AG, Demel RA, de Kruijff S, et al. Aerobic sn-glycerol-3-phosphate dehydrogenase from *Escherichia coli* binds to the cytoplasmic membrane through an amphipathic alpha-helix. *Biochem J*. 2002; 365:471-479.

Myerburg RJ, Castellanos A. Cardiac arrest and sudden cardiac death. In: P. ZD, Libby P, Bonow RO, et al., eds. *Braumwald's Heart disease: A textbook of cardiovascular medicine*. 7th ed. Phildadelphia: Elsevier Saunders; 2005:865-908 (Chapter 33).

Priori SG, Rivolta I, Napolitano C. Genetics of long QT, Brugada, and other channelopathies. In: P. ZD, Jalife J, eds. *Cardiac Electrophysiology. From Cell to Bedside*. 4th ed. Philadelphia: Saunders; 2004:462-470 (Chapter 50).

Sarkozy A, Brugada P. Sudden Cardiac Death and Inherited Arrhythmia Syndromes. *J Cardiovasc Electrophysiol*. 2005; 16:S8-20.

Mohler PJ, Schott JJ, Gramolini AO, et al. Ankyrin-B mutation causes type 4 long-QT cardiac arrhythmia and sudden cardiac death. *Nature*. 2003; 21:634-639.

Corrado 0, Thiene G. Arrhythmogenic right ventricular cardiomyopathy/dysplasia: clinical impact of molecular genetic studies. *Circulation*. 2006; 113:1634-1637.

Schwartz PJ, Priori SG, Dumaine R, et al. A molecular link between the sudden infant death syndrome and the long-QT syndrome. *N Engl J Med. 2000*;343:262-267.

Van Norstrand OW, Valdivia CR, Tester OJ, et al. Molecular and functional characterization of a novel GPD1-L mutations in sudden Infant Death Syndrome. *Circulation* 2007; 116-2253-2259.

Royer A, van Veen TA, Le Bouter S, et al. Mouse model of SCN5A-linked hereditary Lenegre's disease: age-related conduction slowing and myocardial fibrosis. *Circulation*. 2005; 111: 1738-1746.

Tan HL, Bink-Boelkens MT, Bezzina CR, et al. A sodium-channel mutation causes isolated cardiac conduction disease. *Nature*. 2001; 409:1043-1047.

Mihm MJ, Yu F, Cames CA, et al. Impaired myofibrillar energetics and oxidative injury during human atrial fibrillation. *Circulation*. 2001; 104:174-180.

Fukuda K, Davies SS, Nakajima T, et al. Oxidative mediated lipid peroxidation recapitulates proarrhythmic effects on cardiac sodium channels. *Circ Res*. 2005; 97:1262-1269.

Rubart M, Zipes DP. Mechanisms of sudden cardiac death. *J Clin Invest*. 200S; 115:2305-2315.

CAST. Preliminary report: effect of encainide and flecainide on mortality in a randomized trial of arrhythmia suppression after myocardial infarction. The Cardiac Arrhythmia Suppression Trial (CAST) Investigators. *N Engl J Med*.1989; 321 :406-412.

PCT International Search Report and Written Opinion dated Jan. 30, 2009, in International App. No. PCT/US2008/011919 (12 pages).

Krebs et al. (1999). "Na+ translocation by the NADH:ubiquinone oxidoreductase (complex I) from *Klebsiella pneumoniae*." Molecular Microbiology 33(2):590-598.

Udagawa et al. (1986). "Generation of Na+ electrochemical potential by the Na+ -motive NADH oxidase and Na+/H+ antiport system of a moderately halophilic Vibrio costicola." J. Biol. Chem. 261(6):2616-2622.

Sanyal et al., Circulation. Oct. 16, 2007. 116(16) S185-S186, Abstract 941.

Office Action (Restriction Requirement) dated Jul. 6, 2010, in U.S. Appl. No. 12/289,005, filed Oct. 17, 2008.

Office Action dated Oct. 5, 2010, in U.S. Appl. No. 12/289,005, filed Oct. 17, 2008.

Notice of Allowance dated Jun. 23, 2011, in U.S. Appl. No. 12/289,005, filed Oct. 17, 2008.

Office Action dated Oct. 3, 2011, in co-pending U.S. Appl. No. 13/067,953, filed Jul. 11, 2011.

U.S. Appl. No. 13/067,953, filed Jul. 11, 2011.
U.S. Appl. No. 13/091,972, filed Apr. 21, 2011.
U.S. Appl. No. 11/895,883, filed Aug. 27, 2007.
U.S. Appl. No. 13/551,790, filed Jul. 18, 2012.
U.S. Appl. No. 13/585,396, filed Aug. 14, 2012.
U.S. Appl. No. 11/707,882, filed Feb. 20, 2007.
U.S. Appl. No. 13/658,943, filed Oct. 24, 2012.

Office Action dated Oct. 12, 2012, in U.S. Appl. No. 13/091,972, filed Apr. 21, 2011.

Ouzounian et al. Diastolic heart failure: mechanisms and controversies. Nature Clinical Practice Cardiovascular Medicine. 5(7):375-386, Jul. 2008.

Reed et al. FASEB Journal. The senescence-accelerated mouse: a model for the investigation of age-related oxidative stress and diastolic dysfunction. 22:Meeting Abstract Supplement, Mar. 2008, 970. 39 (2 pages).

Li et al. Aging induces cardiac diastolic dysfunction, oxidative stress, accumulation of advanced glycation endproducts and protein modification. Aging Cell. 4(2):57-64, Apr. 2005.

Westermann et al. Cardiac Inflammation Contributes to Changes in the Extracellular Matrix in Patients with Heart Failure and Normal Ejection Fraction. Circulation Heart Failure. 2011;4:44-52.

Satpathy et al. Diagnosis and management of diastolic dysfunction and heart failure. American Family Physician. 73(5):841-846. Mar. 1, 2006.

Kuwahara et al. Transforming Growth Factor-β Function Blocking Prevents Myocardial Fibrosis and Diastolic Dysfunction in Pressure-Overloaded Rats. Circulation; 106:130-135, 2002.

Leask, Andrew. TGF-β, cardiac fibroblasts, and the fibrotic response. Cardiovascular Research. 74:207-212, Jul. 21, 2006.

Reed et al. Diastolic Dysfuntion is Associated with Cardiac Fibrosis in the Senecence-Accelerated Mouse. Circulation 120(18), Supplement 2, S762-S763, Nov. 3, 2009 (1 page).

Blom et al. Gene regulation of connective tissue growth factor: new targets for antifibrotic therapy? Matrix Biology 21 (2002) 473-482.

Kleber AG. Mechanism of Ventricular Arrhythmias: A Perspective. J. Cardiovascular Pharmacology 17(Suppl. 6):S1-S8, 1991.

Salama G et al. Deciphering Arrhythmia Mechanisms—Tools of the Trade. Card Electrophysiol Clin. Mar. 2011; 3(1):11-21 (15 pages).

Moens AL et al. Myocardial ischemia/reperfuion-injury, a clinical view on a complex pathophysiological process. International Journal of Cardiology 100 (2005) 179-190.

Office Action (Restriction Requirement) dated Jun. 11, 2012, in U.S. Appl. No. 12/929,786, filed Feb. 16, 2011.

Office Action dated Sep. 14, 2012, in U.S. Appl. No. 12/929,786, filed Feb. 16, 2011.

U.S. Appl. No. 12/929,786, filed Feb. 16, 2011.

Tu YX, Wernsdorfer A, Honda S, Tomita Y. Estimation of Conduction Velocity Distribution by Regularized-Least-Squares Method. IEEE Trans on Biomedical Engineering. vol. 44, No. 11, Nov. 1997: 1102-1106.

U.S. Appl. No. 14/083,841, filed Nov. 19, 2013.

Office Action dated Oct. 3, 2013, in U.S. Appl. No. 12/929,786, filed Feb. 16, 2011.

Office Action dated Nov. 6, 2013, in U.S. Appl. No. 13/551,790, filed Jul. 18, 2012.

Office Action dated Nov. 6, 2013, in U.S. Appl. No. 13/585,396, filed Aug. 14, 2012.

(56) References Cited

OTHER PUBLICATIONS

Murphy et al. Targeting Antioxidants to Mitochondria by Conjugation to Lipophilic Cations. Annu. Rev. Pharmacol. Toxicol. 2007 47:629-656.
Alexis Biochemicals Catalog pp. 1-48, published Apr. 2007.
http://www.biophysics.org/2010meeting/Registration/RatesDeadlines/tabid/675/Default.aspx.
Liu et al. Mitchondrial dysfunction causing cardiac sodium channel downregulation in cardiomyopathy. *Journal of Molecular and Cellular Cardiology* 54 (2013) 25-34.
Sovari et al. (2013). Mitochondria Oxidative Stress, Connexin43 Remodeling, and Sudden Arrhythmic Death, *Circ Arrhythm Electrophysiol*. 2013;6:623-631 (with Supplemental Material (7 pgs.). Orig. published online Apr. 4, 2013.
Lotrionte et al. Review and Meta-Analysis of Incidence and Clinical Predictors of Anthracycline Cardiotoxicity. *Am J Cardiol* 2013;112:1980-1984.
Mackay et al. Assessment of Anthracycline Cardiomyopathy by Endomycardial Biopsy. Ultrastructural Pathology, 18:203-211, 1994.
Chatterjee et al. Doxorubicin Cardiomyopathy. *Cardiology* 2010;115:155-162.
Angelis et al. Anthracycline Cardiomyopathy Is Mediated by Depletion of the Cardiac Stem Cell Pool and Is Rescued by Restoration of Progenitor Cell Function. *Circulation*. 2010;121:276-292.
Mazevet et al. Complications of chemotherapy, a basic science update. *Presse Med*. 2013; 42; e352-e361.
Octavia et al. Doxorubicin-induced cardiomyopathy: From molecular mechanisms to therapeutic strategies. *Journal of Molecular and Cellular Cardiology* 52 (2012) 1213-1225.
Chanan-Khan et al. Prevention and Management of Cardiotoxicity From Antineoplastic Therapy. *J Support Oncol*. 2004; 2:251-266.
Iravanian et al. Inhibition of Renin-Angiotensin System (RAS) Reduces Ventricular Tachycardia Risk by Altering Connexin43. *J Mol Med* (2011); 89:677-687.
Davies et al. Redox Cycling of Anthracyclines by Cardiac Mitochondria, 1986, *The Journal of Biological Chemistry*, vol. 261, No. 7, 3068-3074.
Felker et al., Underlying Cause and Long-Term Survival in Patients with Initially Unexplained Cardiomyopathy. *The New England Journal of Medicine*, 2000, vol. 342, No. 15, 1077-84.
Octavia Y. et al., Doxorubicin-induced cardiomyopathy: From molecular mechanisms to therapeutic strategies. *Journal of Molecular and Cellular Cardiology*, 52, 2012, 1213-1225.
Guilherme H. et al., Increased Need for Right Ventricular Support in Patients Chemotherapy-Induced Cardiomyopathy Undergoing Mechanical Circulatory Support. *Journal of the American College of Cardiology*, 2014, vol. 63, No. 3, 240-248.
Tabane K. et al. Cancer drugs: Highlighting the molecular mechanisms of cardiotoxicity. SA Heart, 2012;9:244-248.
Zhang S. et al., Identification of the molecular basis of doxorubicin-induced cardiotoxicity. *Nature Medicine*, 2012, vol. 18, No. 11, 1639-1642. With Online Methods (3 pgs).
Ichikawa I. et al., Cardiotoxicity of doxorubicin is mediated through mitochondrial iron accumulation. *Journal of Clinical Investigation*, 2014; vol. 124, No. 2:617-630.
Jeyaseelan R. et al., A novel Cardiac-Restricted Target for Doxorubicin. *The Journal of Biological Chemistry*, 1997, vol. 272, No. 36, 22800-22808.
International Classification of Diseases (ICD) http://www.who.int/classifications/icd/en/ (2 pages) Accessed Jul. 16, 2014.
Cardiomyopathy (I42) and cardiomyopathy due to drug or external agent (I42.7) http://apps.who.int/classifications/icd10/browse/2010/en#/I30-I52 (1 page) Accessed Jul. 16, 2014.
Office Action dated May 14, 2014, in U.S. Appl. No. 12/929,786, filed Feb. 16, 2011.
Office Action dated Jun. 25, 2014, in U.S. Appl. No. 13/551,790, filed Jul. 18, 2012.
Office Action dated Jun. 17, 2014, in U.S. Appl. No. 13/585,396, filed Aug. 14, 2012.
Epstein AE, DiMarco JP, Ellenbogen KA, Estes NA, III, Freedman RA, Gettes LS, Gillinov AM, Gregoratos G, Hammill SC, Hayes DL, Hlatky MA, Newby LK, Page RL, Schoenfeld MH, Silka MJ, Stevenson LW, Sweeney MO, Tracy CM, Epstein AE, Darbar D, DiMarco JP, Dunbar SB, Estes NA, III, Ferguson TB, Jr., Hammill SC, Karasik PE, Link MS, Marine JE, Schoenfeld MH, Shanker AJ, Silka MJ, Stevenson LW, Stevenson WG, Varosy PD. 2012 ACCF/AHA/HRS focused update incorporated into the ACCF/AHA/HRS 2008 guidelines for device-based therapy of cardiac rhythm abnormalities: a report of the American College of Cardiology Foundation/American Heart Association Task Force on Practice Guidelines and the Heart Rhythm Society. *J Am Coll Cardiol* 2013;61:e6-75.
Nakahara S, Tung R, Ramirez RJ, Michowitz Y, Vaseghi M, Buch E, Gima J, Wiener I, Mahajan A, Boyle NG, Shivkumar K. Characterization of the arrhythmogenic substrate in ischemic and nonischemic cardiomyopathy implications for catheter ablation of hemodynamically unstable ventricular tachycardia. *J Am Coll Cardiol* 2010;55:2355-65.
Boriani G, Gasparini M, Lunati M, Santini M, Landolina M, Vincenti A, Curnis A, Bocchiardo M, Padeletti L, Biffi M, Allaria L, Denaro A. Characteristics of ventricular tachyarrhythmias occurring in ischemic versus nonischemic patients implanted with a biventricular cardioverter-defibrillator for primary or secondary prevention of sudden death. *Am Heart J* 2006;152:527-11.
Lindsay BD, Ambos HD, Schechtman KB, Arthur RM, Cain ME. Noninvasive detection of patients with ischemic and nonischemic heart disease prone to ventricular fibrillation. *J Am Coll Cardiol* 1990;16:1656-64.
Rouleau J, Shenasa M, de CJ, Nadeau R. Predictors of survival and sudden death in patients with stable severe congestive heart failure due to ischemic and nonischemic causes: a prospective long term study of 200 patients. *Can J Cardiol* 1990;6:453-60.
Ehlert FA, Cannom DS, Renfroe EG, Greene HL, Ledingham R, Mitchell LB, Anderson JL, Halperin BD, Herre JM, Luceri RM, Marinchak RA, Steinberg JS. Comparison of dilated cardiomyopathy and coronary artery disease in patients with life-threatening ventricular arrhythmias: Differences in presentation and outcome in the AVID registry. *Am Heart J* 2001;142:816-22.
Contractor T, Beni A, Gardiner J, Ardhanari S, Thakur R. Statins reduce appropriate implantable cardioverter-defibrillator shocks in ischemic cardiomyopathy with no benefit in nonischemic cardiomyopathy. *Am J Ther* 2012;19:413-8.
Furushima H, Chinushi M, Okamura K, Komura S, Tanabe Y, Sato A, Izumi D, Aizawa Effect of dl-sotalol on mortality and recurrence of ventricular tachyarrhythmias: ischemic compared to nonischemic cardiomyopathy. *Pacing Clin Electrophysiol* 2007;30:1136-41.
Latif S, Dixit S, Callans DJ. Ventricular arrhythmias in normal hearts. *Cardiol Clin* 2008;26:367-80, vi.
Sadek MM, Marchlinski FE. Ablation of ventricular arrhythmias. *Trends Cardiovasc Med* 2014;24:296-304.
Hoffmayer KS, Gerstenfeld EP. Diagnosis and management of idiopathic ventricular tachycardia. *Curr Probl Cardiol* 2013;38:131-58.
Roberts-Thomson KC, Lau DH, Sanders P. The diagnosis and management of ventricular arrhythmias. *Nat Rev Cardiol* 2011;8:311-21.
Morin DP, Lerman BB. Management of ventricular tachycardia in the absence of structural heart disease. *Curr Treat Options Cardiovasc Med* 2007;9:356-63.
Liu M, Liu H, Jeong EM, Gu L, Dudley SC. Mitochondrial reactive oxygen species regulate the cardiac Na+ channel in heart failure. *Basic Cardiovascular Sciences 2011 Scientific Sessions* 2011;Abstract:2011-A-246-AHA-BCVS.
Rutledge CA, Ng FS, Sulkin MS, Greener ID, Sergeyenko AM, Liu H, Gemel J, Beyer EC, Sovari AA, Efimov IR, Dudley SC. c-Src kinase inhibition reduces arrhythmia inducibility and connexin43 dysregulation after myocardial infarction. *J Am Coll Cardiol* 2014;63:928-34.

* cited by examiner

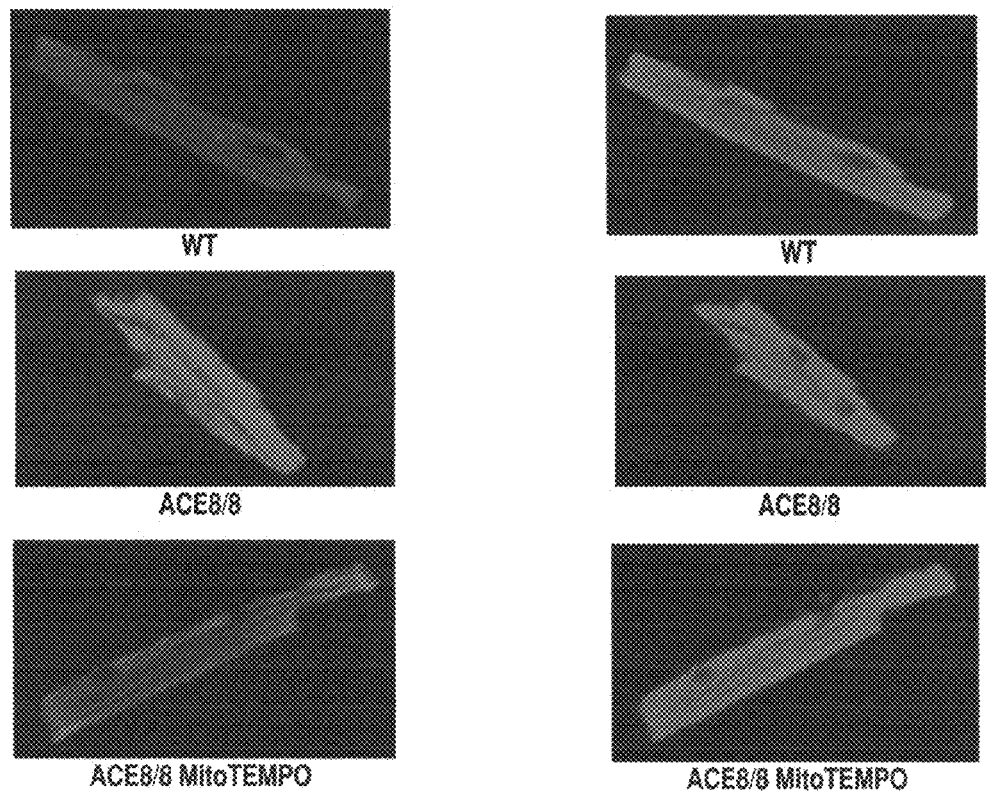
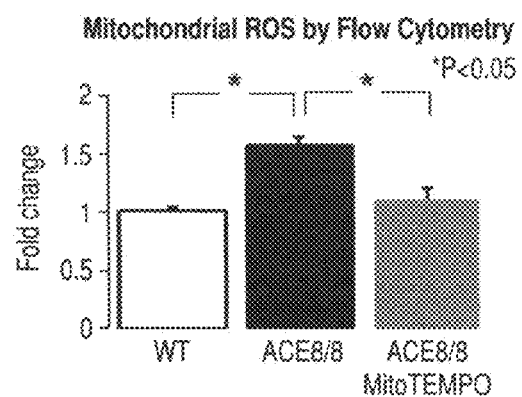
FIG. 2a
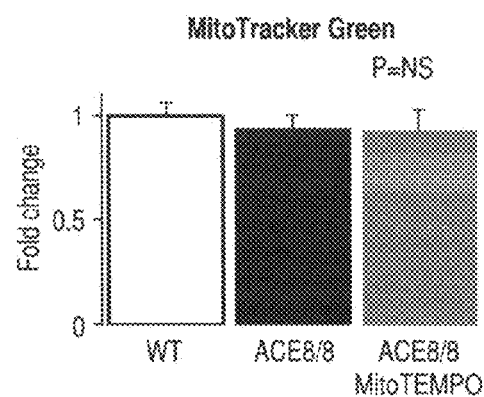
FIG. 2b

US 9,050,350 B2

METHOD FOR MODULATING OR CONTROLLING CONNEXIN 43(CX43) LEVEL OF A CELL AND REDUCING ARRHYTHMIC RISK

CROSS-REFERENCE TO RELATED APPLICATIONS

This is a continuation-in-part (CIP) application of U.S. application Ser. No. 12/929,786, Filed Feb. 16, 2011, which claims the priority benefit of U.S. Provisional Patent Application Ser. No. 61/305,668, filed Feb. 18, 2010, and is a continuation-in-part (CIP) application of U.S. application Ser. No. 12/289,005, filed Oct. 17, 2008, now U.S. Pat. No. 8,003,324B2, which claims the priority benefit of U.S. Provisional Patent Application Ser. No. 60/960,883, filed Oct. 18, 2007, all of the foregoing are hereby incorporated herein in their entirety by reference. This application further claims the priority benefit of U.S. Provisional Patent Application Ser. No. 61/503,096, filed Jun. 30, 2011, which is also hereby incorporated herein in its entirety by reference.

STATEMENT REGARDING FEDERALLY SPONSORED RESEARCH OR DEVELOPMENT

The invention was made with government supported under grants RO1 HL1024025, T32 HL072742, P01 HL058000, RO1 HL106592, a VA MERIT grant, and an American Heart Association Midwest Affiliate Postdoctoral Fellowship # AHA10POST4450037. The government has certain rights in the invention.

FIELD AND BACKGROUND OF THE INVENTION

An increased level of angiotensin-II (AngII), as is found in heart failure, is associated with an increased risk of ventricular tachycardia (VT), and treatment with angiotensin-converting enzyme (ACE) inhibitors and angiotensin receptor blockers reduces that risk (References 1 and 2). Investigating the mechanisms of AngII-induced arrhythmia may result in finding new antiarrhythmic targets. We created a mouse model of cardiac-restricted angiotensin converting enzyme (ACE) overexpression (Reference 3). We demonstrated that homozygous mice (ACE8/8) have a high rate of sudden cardiac death (SCD), with telemetry monitoring showing that approximately 80% of the SCD resulted from VT and less commonly severe bradycardia (Reference 4). The VT and bradycardia were the result of c-Src tyrosine kinase activation, connexin43 (Cx43) reduction, and the impairment of gap junction conduction (References 4-6).

Excess amounts of reactive oxygen species (ROS) have been implicated in the genesis of arrhythmia (References 7-11). The level of ROS is elevated in ACE8/8 mice (Reference 5). ROS is known to activate c-Src (Reference 12). We sought to determine whether ROS mediated any of the Cx43 remodeling during renin-angiotensin system (RAS) activation. Despite considerable evidence that oxidative stress is arrhythmogenic, conventional antioxidants such as vitamin E have not produced impressive therapeutic results in clinical trials (Reference 13). The sources of ROS include the nicotinamide adenine dinucleotide phosphate (NADPH) oxidase activated by AngII and generally requiring the p67 subunit for activity, xanthine oxidase, uncoupled nitric oxide synthase (NOS) in part because of tetrahydrobiopterin depletion, and mitochondria (Reference 14).

In the present invention, the inhibitor therapies were tested to determine the major source of cardiac ROS contributing to arrhythmogenesis in ACE8/8 mice.

ASPECTS OF THE INVENTION

The present disclosure is directed to various aspects of the present invention.

One aspect of the present invention includes discovery and/or demonstration that mitochondrial ROS plays a role in arrhythmogenesis.

Another aspect of the present invention includes discovery and/or demonstration that mitochondrial ROS production is responsible for reduction in Cx43 level in cardiac cells.

Another aspect of the present invention includes discovery and/or demonstration that mitochondrial ROS production is responsible for adversely affecting or reducing ventricular gap function in cardiac cells.

Another aspect of the present invention includes discovery and/or demonstration that mitochondrial ROS production, through a signaling cascade, leads to a reduction in Cx43 level, thereby increasing arrhythmic risk.

Another aspect of the present invention includes discovery and/or demonstration that a mitochondria-targeted antioxidant, such as 2-(2,2,6,6-Tetramethylpiperidin-1-oxyl-4-ylamino)-2-oxoethyl)triphenylphosphonium chloride (Mito-TEMPO), restores the Cx43 to a normal level.

Another aspect of the present invention includes discovery and/or demonstration that a mitochondria-targeted antioxidant, such as 2-(2,2,6,6-Tetramethylpiperidin-1-oxyl-4-ylamino)-2-oxoethyl)triphenylphosphonium chloride (Mito-TEMPO), reduces arrhythmic risk associated with an altered Cx43 level.

Another aspect of the present invention includes discovery and/or demonstration that a mitochondria-targeted antioxidant, such as 2-(2,2,6,6-Tetramethylpiperidin-1-oxyl-4-ylamino)-2-oxoethyl)triphenylphosphonium chloride (Mito-TEMPO), reduces or prevents sudden cardiac death (SCD), or decreases or prevents ventricular tachycardia (VT) inducibility.

Another aspect of the present invention includes suggestions, discovery, demonstration, and/or development of possible therapeutic approaches, strategies, and/or treatment for arrhythmias associated with RAS activation states.

Another aspect of the present invention includes a method of modulating or controlling connexin 43 (Cx43) level of a cell, which includes inducing mitochondrial reactive oxygen species (ROS) production in the cell.

Another aspect of the present invention includes, in a cell having a reduced connexin 43 (Cx43) level, a method of raising the Cx43 level to a normal level, which comprises exposing the cell to an effective amount of a mitochondria-targeted antioxidant. The method can be carried out in vitro or in vivo.

Another aspect of the present invention includes, in a cell having an elevated mitochondrial reactive oxygen species (ROS) production, a method of reducing the ROS production, which comprises exposing the cell to an effective amount of a mitochondria-targeted antioxidant. The method can be carried out in vitro or in vivo.

Another aspect of the present invention includes a method of reducing arrhythmic risk associated with an altered connexin (Cx43) level of a cell, which includes administering a mitochondria-targeted antioxidant to a human or animal in need thereof. The method can be carried out in vitro or in vivo.

Another aspect of the present invention includes a method of preventing sudden cardiac death (SCD) associated with renin-angiotensin system (RAS) activation in a cell, which includes administering a mitochondria-targeted antioxidant to a human or animal in need thereof. The method can be carried out in vitro or in vivo.

Another aspect of the present invention includes a method of controlling or reducing inducibility of ventricular tachycardia (VT) associated with renin-angiotensin system (RAS) activation in a cell, which includes administering a mitochondria-targeted antioxidant to a human or animal in need thereof. The method can be carried out in vitro or in vivo.

Another aspect of the present invention includes a pharmaceutical composition, which includes 2-(2,2,6,6-Tetramethylpiperidin-1-oxyl-4-ylamino)-2-oxoethyl)triphenylphosphonium chloride (MitoTEMPO) and a pharmaceutically acceptable carrier, diluent or excipient.

Another aspect of the present invention includes a therapeutic kit, which includes a pharmaceutical composition including 2-(2,2,6,6-Tetramethylpiperidin-1-oxyl-4-ylamino)-2-oxoethyl)triphenylphosphonium chloride (MitoTEMPO) and a pharmaceutically acceptable carrier, diluent or excipient, and optionally instructions for the use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

One of the above and other aspects, novel features and advantages of the present invention will become apparent from the following detailed description of the non-limiting preferred embodiment(s) of invention, illustrated in the accompanying drawings, wherein:

FIG. 1(a)—RAS-activation mice were treated with the following antioxidants: apocynin, L-NIO, sepiapterin, allopurinol, TEMPOL, and MitoTEMPOL. A group of ACE8/8 mice were also crossed with P67DN mice. Kaplan-Meier survival analysis and log-rank tests show significant improvement in the survival free from sudden arrhythmic death only in the ACE8/8 mice that were treated with Mito-TEMPO. MitoTEMPO had no effect on wild-type mice (WT). FIG. 1(b)—Representative electrocardiograms (ECG lead II) and right ventricular electrograms (endocardial EGM) of WT, ACE8/8 and ACE8/8 mice treated with Mito-TEMPO are shown. VT was induced in 90% of ACE8/8 mice (9 of 10) using a burst pacing protocol starting at 100 ms pacing cycle length (PCL) and decreasing to 30 ms PCL or 2:1 capture. Treatment with MitoTEMPO reduced VT inducibility in ACE8/8 mice to 17% (one of six mice) using the same above pacing protocol (P<0.05);

FIGS. 2a-b illustrate that mitochondrial ROS is increased in RAS Activation. FIG. 2(a)—Mitochondrial ROS was measured using MitoSOX fluorescence. Representative confocal microscopy images show an increase in the mitochondrial superoxide level in ACE8/8 cardiomyocytes and suppression of that level with MitoTEMPO treatment. Flow cytometry analysis shows a 1.5 fold increase in the level of mitochondrial superoxide in ACE8/8 mice and MitoTEMPO decreased that level to normal. FIG. 2(b)—MitoTracker Green was used to quantify mitochondria. There is no significant difference among the control, ACE8/8 and ACE8/8 treated with Mito-TEMPO groups (n=10 for each group, P=NS) in mitochondrial number;

FIG. 4(a) Mito-TEMPO increases the total Cx43 level in ACE8/8 mice from 24% to 62% of the Cx43 level in the control mice (P<0.05). FIG. 4(b) Immunohistochemistry staining for Cx43 confirms the increase in Cx43 level in ACE8/8 mice by MitoTEMPO treatment;

DETAILED DESCRIPTION OF THE PREFERRED EMBODIMENT(S) OF THE INVENTION

Figures 1A, 1B:
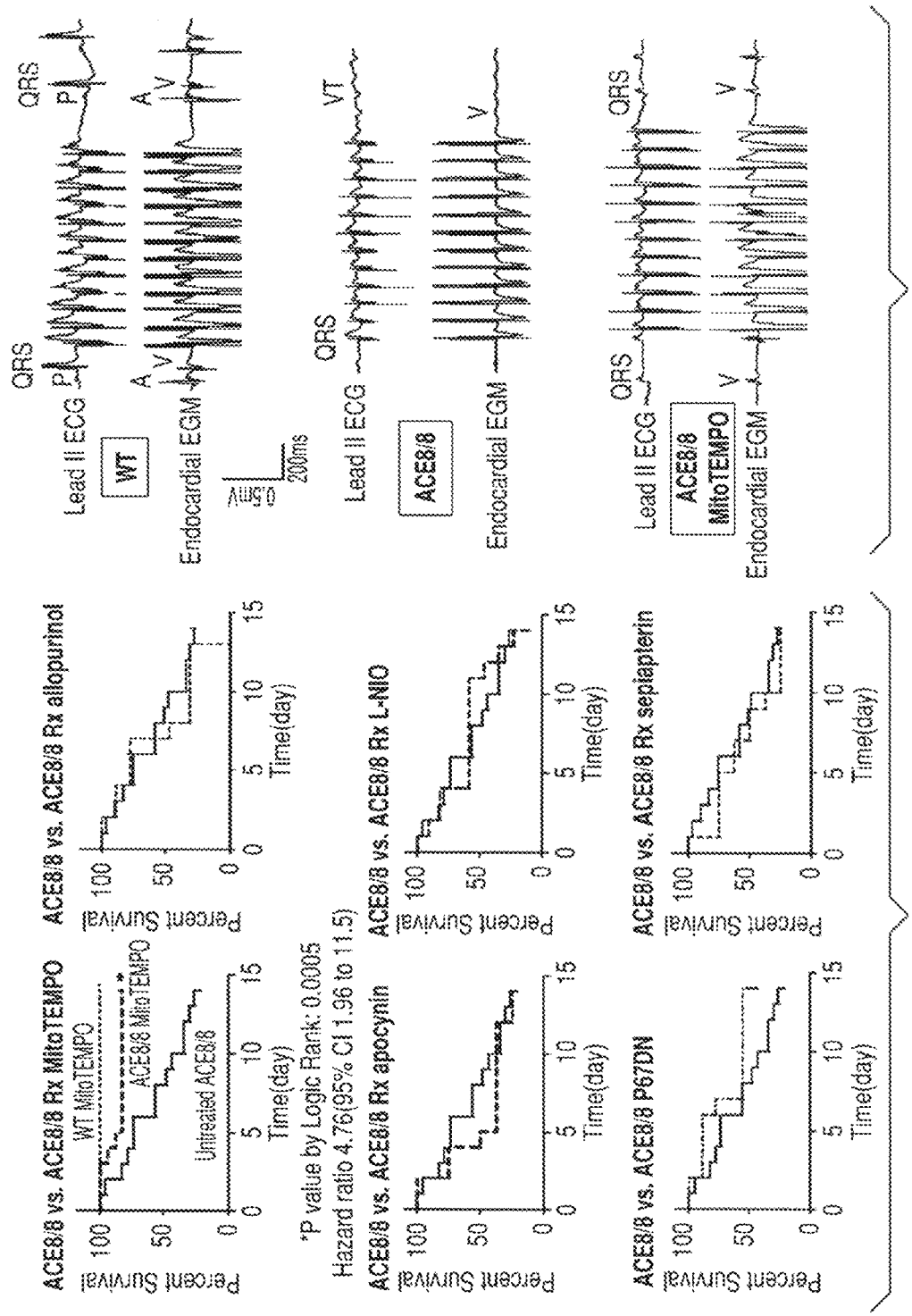
FIGS. 1a-b illustrate that a mitochondrial antioxidant inhibits sudden cardiac death and ventricular arrhythmia inducibility.

Previously, it was shown that a mouse model (ACE8/8) of cardiac renin-angiotensin system (RAS) activation has a high rate of spontaneous ventricular tachycardia (VT) and sudden cardiac death (SCD) secondary to a reduction in connexin43 (Cx43) level. Angiotensin-II activation increases reactive oxygen species (ROS) production, and these mice show cardiac oxidation. Here, it is determined that the source of ROS and that ROS played a role in the arrhythmogenesis.

In particular, the present invention is based, at least in part, on the discovery and/or demonstration that an ROS overproduction leads to a reduction in connexin 43 (Cx43) level in cardiac cells.

Wild-type and ACE8/8 mice with and without two weeks of treatment with L-NIO (nitric oxide synthase inhibitor), sepiapterin (precursor of tetrahydrobiopterin), MitoTEMPO (mitochondria-targeted antioxidant), TEMPOL (a general antioxidant), apocynin (NADPH oxidase inhibitor), allopurinol (xanthine oxidase inhibitor), and ACE8/8 crossed with P67 dominant negative mice to inhibit the NADPH oxidase were studied. Western blotting, detection of mitochondrial ROS by MitoSOX Red, electron microscopy, immunohistochemistry, fluorescent dye diffusion technique for functional assessment of Cx43, and in-vivo electrophysiology study were performed. Treatment with MitoTEMPO reduced SCD in ACE8/8 mice (from 74% to 18%, P=0.0005), decreased VT inducibility (from 90% to 17%, P<0.05), diminished elevated mitochondrial ROS to the control level, prevented structural damage to mitochondria, resulted in 2.6 fold increase in Cx43 level at the gap junctions, and corrected gap junction conduction. None of the other antioxidant therapies prevented VT and SCD in ACE8/8 mice.

Methods

The animal experiments were conducted according to the National Institutes of Health (NIH) Guide for the Care and Use of Experimental Animals and were approved by the University of Illinois Institutional Animal Care and Use Committee. A group of wild-type mice (n=10) with similar background to the ACE8/8 mice (C57BL), and the following groups of ACE8/8 mice were studied:
1. ACE8/8 mice untreated control (n=23).
2. ACE8/8 mice treated with 4'-hydroxy-3' methoxyacetophenone (apocynin) (Sigma-Aldrich, St. Louis, Mo.) to inhibit the NADPH oxidase activity (Reference 15) (1.5 mmol/L in drinking water for two weeks, n=8).
3. ACE8/8 mice crossed with a P67 dominant negative (P67DN) mice to inhibit NADPH oxidase activity (n=10). P67 is an important subunit of NADPH oxidase (Reference 16).
4. ACE8/8 mice treated with N5-(1-iminoethyl)-L-ornithine, dihydrochloride (L-NIO) (Sigma-Aldrich) to inhibit nitric oxide synthase (NOS) (25 mg/Kg/d intraperitoneal injections for two weeks, n=10). L-NIO is an inhibitor of all NOS subtypes (Reference 17).
5. ACE8/8 mice treated with 2-amino-7,8-dihydro-6-(2S-hydroxy-1-oxopropyl)-4(1H)-pteridinone (sepiapterin) (Reference 18) (Sigma-Aldrich), a precursor of tetrahydrobiopterin, to prevent eNOS uncoupling without inhibition of NOS (5 mg/Kg/d intraperitoneal injections for two weeks, n=8).
6. ACE8/8 mice treated with 1,5-dihydro-4H-pyrazolo[3,4-d]pyrimidin-4-one (allopurinol) (Reference 19) (Sigma-Aldrich) to inhibit xanthine oxidase (1 mmol/L in the drinking water for two weeks, n=10).
7. ACE8/8 mice treated with 4-hydroxy-2,2,6,6-tetramethylpiperidinyloxy (TEMPOL) (Enzo Life Sciences), which is a general antioxidant and mimetic of superoxide dismutase (Reference 20) (2 mmol/L in drinking water for two weeks, n=8).
8. ACE8/8 mice treated with (2-(2,2,6,6-Tetramethylpiperidin-1-oxyl-4-ylamino)-2-oxoethyl)triphenylphosphonium chloride (MitoTEMPO) (Reference 21) (Enzo Life Sciences, Plymouth Meeting, Pa.) to target mitochondrial superoxide (0.7 mg/Kg/d intraperitoneal injections for two weeks, n=17).

In addition, a group of wild-type mice were treated with MitoTEMPO (0.7 mg/Kg/d intraperitoneal injections for two weeks, n=5) to evaluate for any possible harmful effects of treatment.

Survival Recording and Analysis

Survival of all treated and untreated groups were recorded every morning during the two weeks of treatment and/or observation. Survival was assessed by using Kaplan-Meier analysis and log rank tests.

Electrophysiology Study

For the electrophysiology studies, the control mice (n=5), ACE8/8 mice (n=10) and ACE8/8 mice treated with MitoTEMPO (n=6) were anesthetized with an intraperitoneal injection of ketamine (100 mg/kg) and xylazine (5 mg/kg). As it was previously described (Reference 4), after cutdown of the right internal jugular vein, a 1.1-F catheter with 0.5-mm inter-electrode spacing (EPR 800, Millar Instruments, Houston, Tex.) was placed into the vein and was advanced into the right ventricle. A constant current stimulator (A320, World Precision Instruments, Sarasota, Fla.) connected to a computer was used for cardiac stimulation. During the experiment, body temperature was maintained at 37° C. with a warming pad. Burst pacing at cycle lengths of 100 to 30 ms (or to the loss of 1:1 capture) was used to test for VT inducibility. A rhythm with more than three consecutive ventricular beats was considered to be VT.

Mitochondrial ROS Measurement by Confocal Microscopy

To measure mitochondrial ROS, the fluorescent probe MitoSOX Red was used as previously described (Reference 22). Briefly, cardiomyocytes were isolated from control, ACE8/8 or ACE8/8 mice treated with MitoTEMPO (n=3 for each group) as previously described (Reference 22). Cells were stained with 5 µM MitoSOX Red and 100 nM MitoTracker Green for 10 minutes at 37° C., followed by washing twice with warm MEM medium and were incubated for 10 minutes. Images were taken by a Zeiss LSM510 META confocal microscope (Carl Zeiss GmbH, Oberkochen, Germany) using an argon laser excitation (488 nm and 514 nm) with emission collection through a 560-nm long-pass filter. Images were captured using 63× water immersion objective lens at 1024×1024 pixels. Cell area was calculated, and the whole-cell fluorescence intensity of MitoSOX Red was measured with ImageJ software (NIH). The number of pixels of the cell fluorescence divided by the cell area was used to determine the mitochondrial ROS generation.

Mitochondrial ROS Measurement by Flow Cytometry

To quantify the mitochondrial ROS by flow cytometry, the measurements were carried out using Cyan ADP (Beckman Coulter, Brea, Calif.). Isolated cardiomyocytes from each group (n=3 animals for each group) were stained with 5 µM MitoSOX Red with a similar method as above. MitoSOX Red was excited by laser at 488 nm, a similar excitation (514 nm) used in confocal studies, and the data were collected for the FSC, SSC, pulse-width, and 585/42 nm (FL2) channels. Cell debris as represented by distinct, low forward and side scatter were gated out for analysis. The data are presented by histogram of mean intensity of MitoSOX fluorescence or fold change when compared with an unstained control with MitoSOX present.

Transmission Electron Microscopy

Control, ACE8/8 mice, and ACE8/8 mice treated with MitoTEMPO were studied (n=3 for each group). Tissues were washed with cold phosphate buffered saline (PBS), and fixed with EM Grade glutaraldehyde 4% in 0.1M cacodylate buffer (pH 7.4). Fixed tissues were incubated with osmium tetroxide 1% in cacodylate buffer for 2 h and processed for embedding. Ultra-thin sections were cut 83 nm, placed on 200 mesh copper grids, and stained with uranyl acetate and lead citrate. All materials were purchased from Electron Microscopy Sciences (Hatfield, Pa.). Samples were visualized using a JEM-1220 Jeol transmission electron microscopy (JEM, Peabody, Mass.), and micrographs were taken using a Gatan Digital Micrograph (Gatan Microscopy, Plesanton, Calif.). All microscopy measurements were performed using the University of Illinois Central Microscopy Research Core Facility. Random images (n=20) from each sample were taken for analysis. The area occupied by mitochondria and the ratio of the damaged area identified by white blank areas to the area of the whole mitochondrion were measured using a digital grid that was placed over each micrograph (15×15 grid with 225 points at cross sections). The points that fell within a mitochondrion were counted and were divided by the total number of points (i.e. 225 minus pseudospaces) to measure the area occupied by mitochondria. The total points of white areas within a mitochondrion were divided by the total points that fell within the mitochondrion to estimate the damage.

Western Blot Analysis

The control, ACE8/8, and ACE8/8 treated with MitoTEMPO mice (n=5 for each group) were sacrificed, and their hearts were excised. The ventricular tissue was homogenized in a buffer containing 20 mM of tris-(hydroxymethyl)-aminomethane (Tris-Cl) (pH, 7.4), 150 mM of sodium chloride (NaCl), 2.5 mM of ethylenediaminetetraacetic acid (EDTA), 1% Triton-100, 10 µL/mL of phenylmethylsulfonyl fluoride (PMSF), 10 µL/mL of protein inhibitor cocktail (Pierce, Rockford, Ill.), and 10 µL/mL of phosphatase inhibitor cocktail II (Sigma-Aldrich, St. Louis, Mo.). Protein samples (5 to 20 µg) were separated via 10% sodium dodecyl sulfate polyacrylamide gel electrophoresis (SDS-PAGE) and were transferred to nitrocellulose membranes. The membranes were blotted with the primary antibodies against phosphorylated (Tyr 416) c-Src and Cx43 (Cell Signaling, Danvers, Mass.). For a loading control, the membranes were blotted with a primary antibody against glyceraldehyde-3-phosphate dehydrogenase (GAPDH; Santa Cruz Biotech, Santa Cruz, Calif.). After treatment with secondary anti-rabbit or anti-mouse antibodies, imaging was performed with enhanced chemiluminescence. The radiographic film images were scanned and analyzed with NIH ImageJ software. Cx43 and phospho-Src levels were corrected for the GAPDH level for each sample.

Immunohistochemistry

Control, ACES/8, and ACES/8 treated with MitoTEMPO mouse hearts (n=4 for each group) were fixed in 10% formalin. After which, 8-µm thick sections were blocked for 1 h at room temperature and then were incubated with anti-Cx43 antibodies (Cell Signaling) overnight at 4° C. at concentrations known to provide the best signal-to-noise ratio. The slides were reviewed with a Zeiss Axioskop microscope (Carl Zeiss, Inc, Thornwood, N.Y.), and photomicrographs with original magnification ×40 were taken from the apex, the mid-left ventricle (LV), and the LV base. From each of those sites, photomicrographs were taken from the endocardium and epicardium. The Cx43 content was quantified with the use of a grid that divided the field of view into 225 squares. At the intersection points aligning with the intercalated disks, Cx43 was scored as "1" (present) or "0" (absent). The results were expressed as the percentage occupied by Cx43 of the total area examined, excluding pseudospaces. This method has been used previously to quantify levels of collagen and Cx43 in cardiac tissue (References 4, 23 and 24).

Functional Assessment of Cx43

An established technique was used for measuring Cx43 function that involves fluorescent dye introduction and diffusion in intact heart muscle (References 4 and 25). Fresh hearts from control, ACES/8 and ACES/8 mice treated with MitoTEMPO (n=5 for each group) were obtained. A sample from each heart was placed in phosphate buffered saline at 37° C., the anterior surface of the left ventricle was punctured with a 27-gauge needle, and the sample was incubated with a droplet of 0.5% Lucifer yellow (LY) and a droplet of 0.5% Texas Red Dextran (TRD) in 150 mM of LiCl solution. After a 15-minute incubation, the samples were fixed in 4% formaldehyde for 30 min, washed in phosphate-buffered saline, frozen in liquid nitrogen, and sliced into 14-µm sections. The sections were mounted on microscope slides and examined on a Leica DM5000 B epifluorescence microscope (Leica Microsystems Inc., Bannockburn, Ill.). Digital images of the spread of LY and TRD were obtained. The measurement of the dye spread was performed with ImageJ software. Molecules of TRD are too large to traverse gap junctions and stain cells with disrupted sarcolemmal membranes. The TRD distribution was subtracted from the length of the LY spread at the same site to measure the true LY spread through gap junctions. Dye spread in longitudinal and transverse directions was assessed.

Statistical Analysis

The values are presented as the mean±the SEM. The t test, one-way analysis of variance with post hoc tests of significance, the Tukey honestly significant test, and the Fisher exact test for 2×2 tables were used where appropriate, and a P value of <0.05 was considered statistically significant. The survival data were analyzed with the Kaplan-Meier method, and the P value was calculated with the log-rank test. The correlation was assessed with the Pearson correlation coefficient method.

Results

Figure 1C:
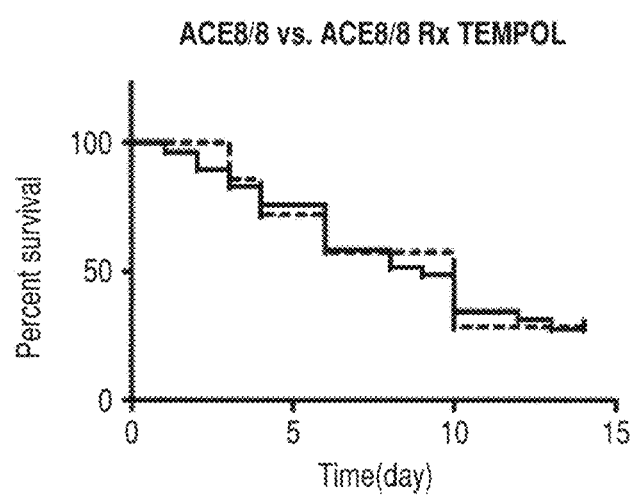
FIG. 1c illustrates that a general antioxidant did not improve survival. Kaplan-Meier survival analysis shows no improvement in the survival from sudden arrhythmic death in ACE8/8 mice treated with TEMPOL.

Mitochondria-Targeted Antioxidant Therapy Prevented Sudden Cardiac Death and Inducibility of Ventricular Tachycardia The survival of all animals was recorded daily, and a survival analysis was performed with the Kaplan-Meier test. Only treatment with MitoTEMPO prevented SCD and improved survival in the ACE8/8 mice from 26% to 82% (95% Cl, 1.96 to 11.53; P<0.005). Although NADPH oxidase, xanthine oxidase, and uncoupled NOS are sources of increased cardiac ROS with RAS activation, none of the other antioxidant therapies was effective in prevention of SCD (FIG. 1a). Treatment with TEMPOL, a general antioxidant, was not associated with improvement of survival free of sudden arrhythmic death (FIG. 1c). Treatment of control mice with MitoTEMPO did not cause any death or gross abnormality in those mice.

In electrophysiology studies, VT was induced in 90% (nine of 10) of ACE8/8 mice with a mean pacing cycle length (PCL) of 44 ms. The induced VTs in the ACE8/8 mice were primarily monomorphic (88%); this suggests a predominant reentry mechanism for the VT episodes. VT inducibility was decreased from 90% to 17% (one of six) in ACE8/8 mice by MitoTEMPO treatment (P<0.05) (FIG. 1 by VT could not be induced in control mice.

RAS Activation Increased Mitochondrial Superoxide Levels

Quantification of mitochondrial ROS levels by the MitoSOX reduction and flow cytometry methods revealed a 1.5-fold increase in the mitochondrial superoxide level in the ACE8/8 mice compared to the control mice (p<0.05) (FIG. 2a). MitoTEMPO treatment reduced mitochondrial ROS level to 1.1-fold of that in the control mice (P=NS) (FIG. 2a). Quantification of mitochondria by MitoTracker Green did not show any significant change between those groups (FIG. 2b).

MitoTEMPO Reversed Mitochondrial Damage in RAS Activation

Figure 3:
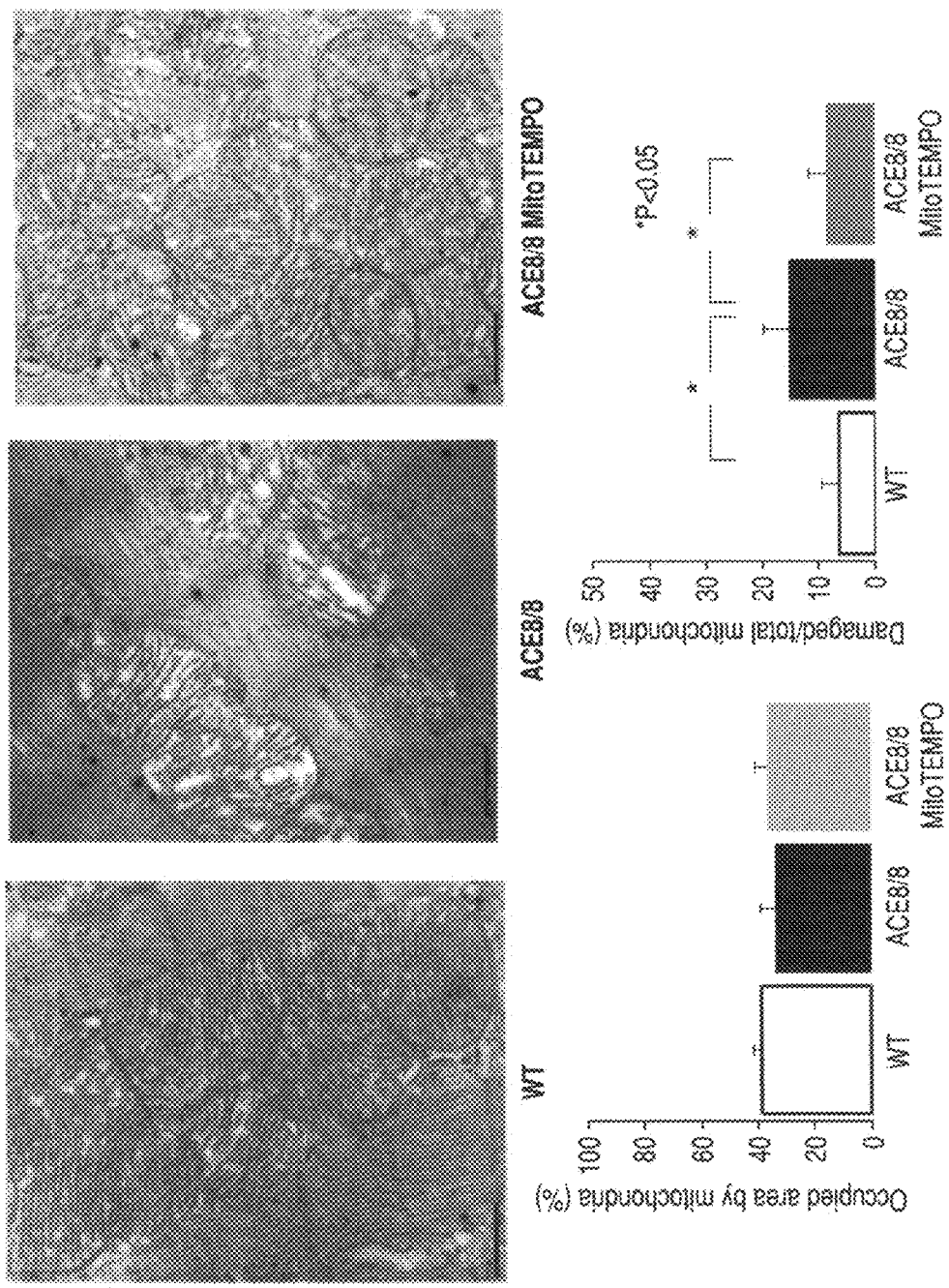
FIG. 3 illustrates that RAS Activation was associated with mitochondrial injury. Electron microscopy shows damage to the inner membrane and cisterna of mitochondria and vacuous areas within mitochondria areas with RAS activation that are prevented by MitoTEMPO treatment. RAS activation did not significantly change the percent area occupied by mitochondria compared with the control (38±2%, 34±5%, 36±4% of cytoplasmic surface area, for control, ACE8/8, Mito-TEMPO groups, respectively; P=NS), a finding consistent with the MitoTracker Green analysis.

The percent of the cytoplasmic area occupied by mitochondria was not statistically different among the groups studied, consistent with mitochondria quantification with MitoTracker Green (FIG. 3). Nevertheless, by electron microscopy, ACE8/8 mice showed significant damage to the mitochondria inner membrane and cisterna (FIG. 3). The damaged area identified by the ratio of vacuous area within a mitochondrion to the whole mitochondrion was significantly higher in the ACE8/8 than in the control mice. This ratio was ameliorated by MitoTEMPO treatment (6.5±3%, 15±4%, and 8.5±3% in the control, the ACE8/8, and the ACE8/8 mice treated with MitoTEMPO, respectively; P<0.05 for control compared to ACE8/8 mice). In electron microscopy study, rarely could gap junctions be identified in untreated ACE8/8 cardiomyocytes.

MitoTEMPO Increased Connexin43 Levels at the Gap Junctions

Figure 4:
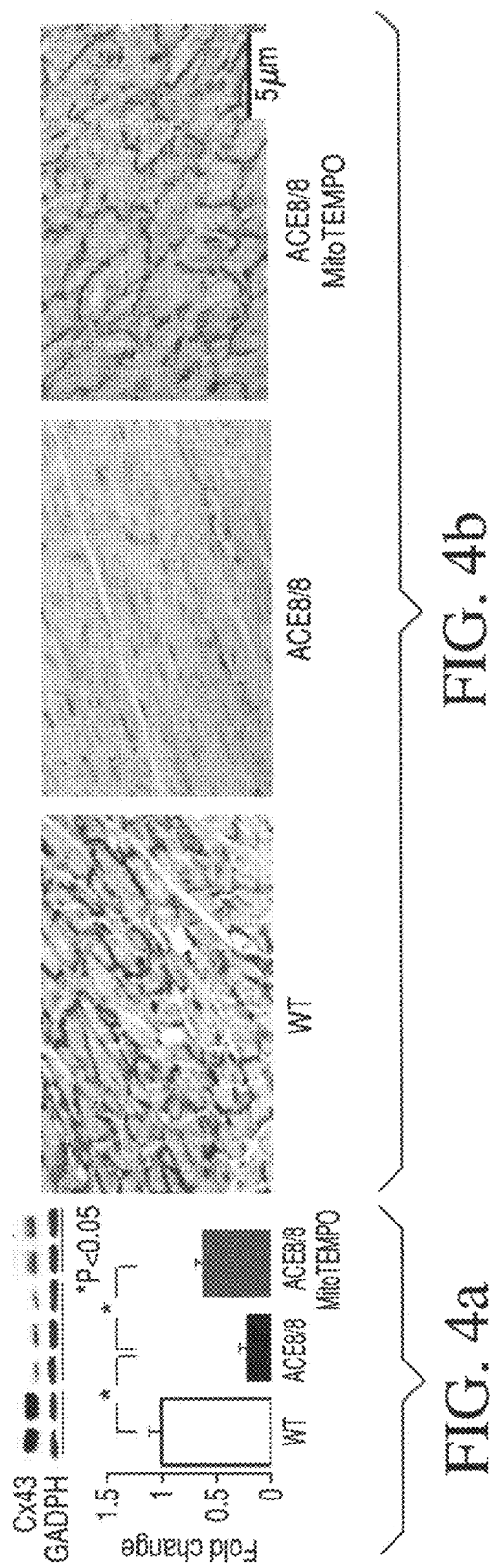
FIGS. 4a-b illustrate that a mitochondrial antioxidant recovers Cx43 in RAS-activation mice.

The total Cx43 level detected by Western blot was decreased in ACE8/8 mice to 24% of control (P<0.05), and MitoTEMPO treatment increased that to 62% of control (P<0.05) (FIG. 4a).

Figure 2C:
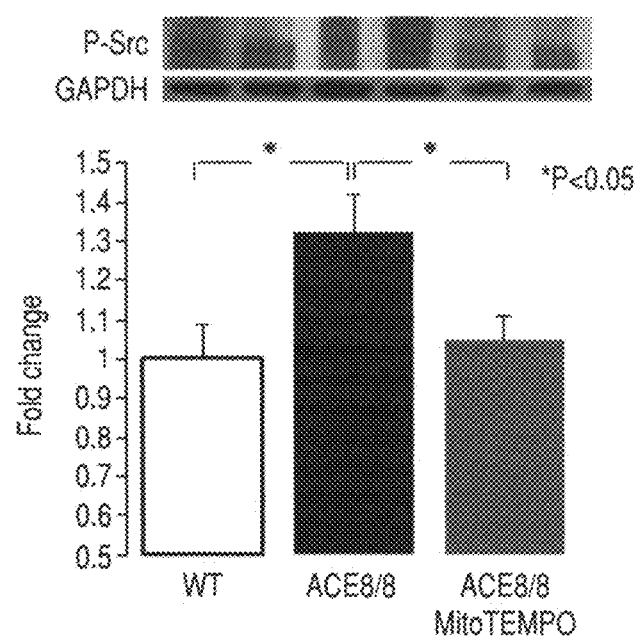
FIG. 2c illustrates that MitoTEMPO prevents activation of c-Src by RAS activation. Western blot analysis shows the level of phospho-(Tyr416) Src (active c-Src) is 32% higher in ACES/8 than in control mouse hearts (P<0.05), and reduces to the level of control after Mito-TEMPO treatment (n=5 for each group, P=NS)

Immunohistochemistry staining showed that the Cx43 level in ACE8/8 mice was decreased to a comparable level measured by Western blot, and most of the remaining Cx43 in the untreated ACE8/8 mice was no longer located at identifiable intercalated disks (FIG. 4b). The level of active c-Src, phospho-(Tyr416), was 32% higher in ACE8/8 than in control mouse hearts, and it was reduced to that of control mice by MitoTEMPO treatment (P=NS compared to control) (FIG. 2c).

MitoTEMPO Increased Gap Junction Conduction to the Control Level

Figure 5:
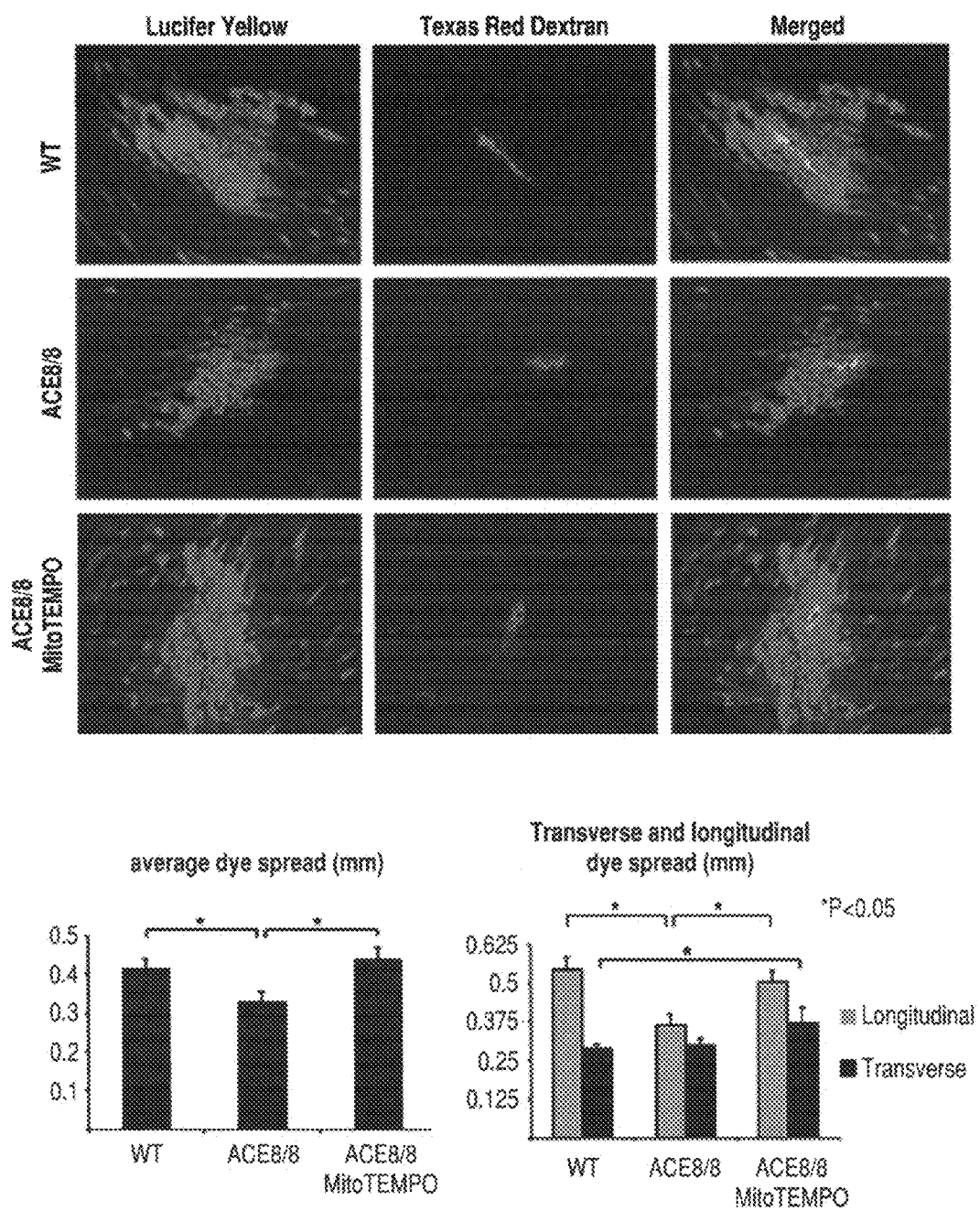
FIG. 5 illustrates that Cx43 function is Improved with a Mitochondrial Anti-Oxidant. Cx43 functional assessment by the fluorescent dye diffusion technique reveals an increase in dye spread in ACE8/8 mouse hearts with MitoTEMPO treatment.

Functional assessment of Cx43 was done by using a fluorescent dye diffusion technique (FIG. 5). The gap junction dye diffusion in longitudinal direction was reduced in the untreated ACE8/8 mice to 62% of that in the control mice (P<0.05). MitoTEMPO treatment returned the gap junction conduction to the normal range (P=NS compared to control).

Discussion

Cx43 is the major structural protein of ventricular gap junctions, and a significant decrease in Cx43 causes sudden death (Reference 26). Here, it is shown that cardiac RAS activation, as occurs in heart failure (References 1 and 27), was associated with a significant reduction in Cx43. This range of reduction in Cx43 is known to be arrhythmogenic (References 28 and 29). It was previously shown that c-Src mediates the reduction of Cx43 by AngII (Reference 4). The current experiments show that mitochondrial ROS plays a central role in the AngII-mediated Cx43 remodeling probably by ROS activation of c-Src (References 30 and 31).

Although ROS have been implicated in the genesis of arrhythmia, the best strategy to effectively reduce the level of ROS in order to prevent arrhythmia is not known. In this study, only a mitochondria-targeted antioxidant was able to prevent arrhythmia. Targeting other known ROS sources or using a general antioxidant was ineffective. This result, particularly the therapeutic difference between TEMPOL and MitoTEMPO treatments, suggests that AngII-mediated ROS production is highly compartmentalized within mitochondria in cardiomyocytes. It has been recently shown that AngII receptors exist on the mitochondrial inner membrane (Reference 32), and AngII may affect directly mitochondrial ROS production. In addition, an isoform of the NADPH oxidase (NOX4) exists in mitochondria (References 33 and 34), and AngII is known to activate NADPH oxidase (References 35 and 36). While our experiments do not suggest a role for the NADPH oxidase, NOX4 does not require P67 subunit for its activation (Reference 37), and apocynin may not effectively inhibit mitochondrial NOX4-dependent ROS production. Therefore, it is possible that this system could be involved in what appears to be AngII signaling directly to mitochondria without NADPH oxidase involvement, possibly through a ROS-induced-ROS mechanism (References 38 and 39).

This study does not preclude the possibility of other sources of ROS contributing to arrhythmogenesis in other cardiac pathological states. It has been shown that perfusion of the whole heart or isolated cardiomyocytes with $H_2O_2$ is arrhythmogenic, which highlights the importance of ROS production in arrhythmogenesis independent of the source of ROS (References 24 and 40). Our results may simply be a function of the relative amounts of the enzymatic ROS sources in a cardiomyocyte. Consistent with others (Reference 9), we found that more than 30% of the cardiomyocyte area was occupied by mitochondria, and these mitochondria were damaged by RAS activation. Similar findings of the importance of mitochondria as a source of ROS and accompanying mitochondrial damage were recently reported in other cardiac pathologies such as heart failure, a RAS activation state (References 9, 41 and 42).

Figure 6:
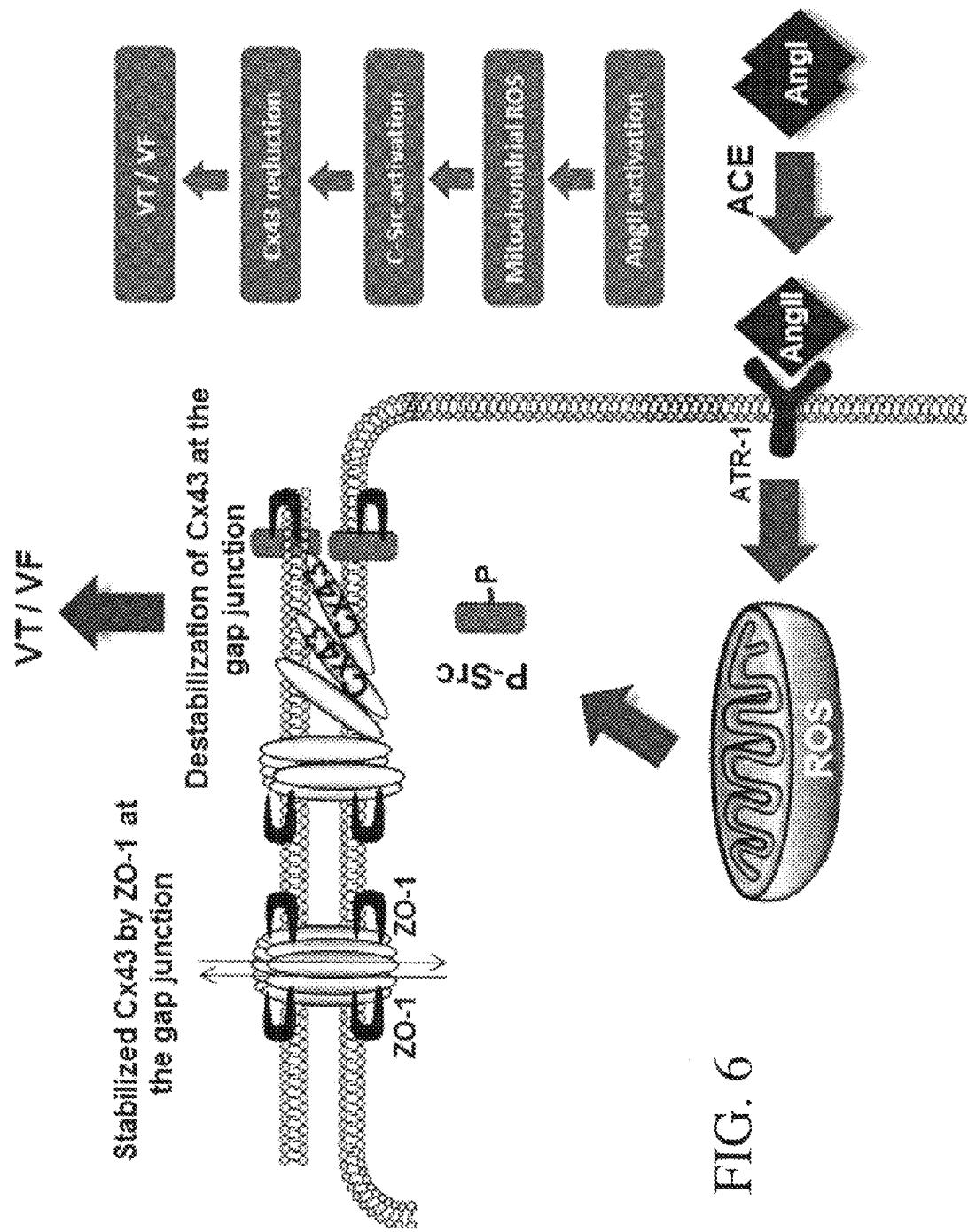
FIG. 6 illustrates a proposed signaling cascade of RAS-induced arrhythmogenesis. Activation of AngII significantly increases mitochondrial ROS production which in turn activates c-Src and results in Cx43 reduction at the gap junctions. Impaired gap junction conduction provides substrate for ventricular arrhythmia and sudden arrhythmic death.

Previously, it was shown that RAS activation reduced Cx43 and that gap junction impairment was the main substrate for slow conduction and ventricular arrhythmia (Reference 6). It was demonstrated that c-Src inhibition prevented Cx43 reduction and SCD (Reference 4). Here, it is shown that mitochondrial ROS inhibition reduced c-Src activation, suggesting a model of RAS induced activation, as shown in FIG. 6. The findings herein collectively can be explained by a signaling cascade where cardiac RAS activation increases mitochondrial ROS production and mitochondrial injury, activates c-Src, reduces Cx43 at intercalated disks through competition with activated c-Src, reduces gap junction function, and increases ventricular arrhythmias.

These results may have clinical implications in patients with heart failure because AngII and ROS are elevated (References 1, 27 and 43-46) and Cx43 is reduced in this condition, which is associated with increased sudden death (References 47 and 48). Moreover, the proposed signaling cascade could explain why angiotensin converting enzyme inhibitors and AngII receptor blockers decrease sudden death (References 1 and 44). In addition, these results may have clinical implications in pathological conditions with elevated levels of ROS and c-Src activation due to insults other than AngII, for example, in cardiac ischemia and in ischemia-reperfusion state (References 49 and 50). Nevertheless, a gene-targeted model of cardiac-restricted RAS activation was used, and the result may vary in systemic elevation of AngII. It is also possible that MitoTEMPO exerted part of its antiarrhythmic effects by mechanisms other than c-Src activation and Cx43 remodeling. On the other hand, the lack of ventricular fibrosis, a normal cardiac sodium current, and an unchanged ventricular effective refractory period in the ACES/8 mice at the age they were studied (References 3 and 5) support a major role for mitochondrial ROS in RAS-mediated Cx43 remodeling.

In summary, it was found that RAS activation resulted in mitochondrial injury, mitochondrial ROS production, a reduction in Cx43, and increased arrhythmic risk. These changes were ameliorated by a mitochondria-targeted antioxidant, but not agents targeted to other sources of cardiac oxidation or a general antioxidant. These results point out the importance of targeting specific ROS sources to increase therapeutic effectiveness and identify a possible new treatment for arrhythmias associated with RAS activation states.

From the above, it is concluded that mitochondrial oxidative stress plays a central role in angiotensin II-induced gap junction remodeling and arrhythmia, and that mitochondria-targeted antioxidants may be effective antiarrhythmic drugs in cases of RAS activation.

The invention also provides pharmaceutical or dietary supplemental compositions comprising 2-(2,2,6,6-Tetramethylpiperidin-1-oxyl-4-ylamino)-2-oxoethyl)triphenylphosphonium chloride (MitoTEMPO). Accordingly, the compound (2-(2,2,6,6-Tetramethylpiperidin-1-oxyl-4-ylamino)-2-oxoethyl)triphenylphosphonium chloride (Mito- TEMPO)), can be formulated for oral or parenteral administration for the therapeutic or prophylactic treatment of diseases or conditions associated with arrhythmogenesis, particularly associated with reduced connexin 43 level.

By way of illustration, the compound can be admixed with conventional pharmaceutical carriers and/or excipients and used in the form of tablets, capsules, elixirs, suspensions, syrups, wafers, and the like. Such pharmaceutical compositions contain from about 0.1 to about 90% by weight of the active compound (2-(2,2,6,6-Tetramethylpiperidin-1-oxyl-4-ylamino)-2-oxoethyl)triphenylphosphonium chloride (Mito-TEMPO)), and more generally from about 10 to about 30%. The pharmaceutical compositions may contain common carriers and excipients, such as corn starch, gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent.

Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration. A typical composition for intramuscular or intrathecal administration consists of a suspension or solution of active ingredient in an oil, for example arachis oil or sesame oil. A typical composition for intravenous or intrathecal administration consists of a sterile isotonic aqueous solution containing, for example active ingredient and dextrose or sodium chloride, or a mixture of dextrose and sodium chloride. Other examples of aqueous solution are lactated Ringers injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of the invention which are active on rectal administration can be formulated as suppositories. A typical suppository formulation will generally consist of active ingredient with a binding and/or lubricating agent such as a gelatin or cocoa butter or other low melting vegetable or synthetic wax or fat.

The active compound is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like. Suitable doses are selected to effect a blood concentration of about 100-300 µM, preferably 100 µM.

According to the invention, a compound can be administered in a single daily dose or in multiple doses per day. The treatment regimen may require administration over extended periods of time, for example, for several days, for from one to six weeks, or longer.

Suitable formulations for use in the present invention can be found in Remington's Pharmaceutical Sciences, Mace Publishing Company, Philadelphia, Pa., 17th ed. (1985).

The compositions of the present invention can be used to treat conditions associated with RAS activation, including all disease states and/or conditions that are acknowledged now, or that are found in the future, to be associated with the activity of connexin 43 levels. Such disease states include, but are not limited to, pathophysiological disorders, including hypertension, cardiac arrhythmogenesis, sudden cardiac death (SCD), ventricular tachycardia (VT), insulin-dependent diabetes, non-insulin dependent diabetes mellitus, diabetic neuropathy, seizures, tachycardia, ischemic heart disease, cardiac failure, angina, myocardial infarction, ventricular fibrillation, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, subarachnoid hemorrhage, Alzheimer disease, drug dependence/addiction, schizophrenia, Huntington's chorea, tension-type headache, trigeminal neuralgia, cluster headache, migraine (acute and prophylaxis), inflammatory pain, neuropathic pain and depression.

In a preferred embodiment, the compound of the present invention is used to reduce arrhythmic risk, including heart failure, (SCD) and ventricular tachycardia (VT). As previously mentioned, arrhythmic risk is associated with a reduction in the connexin 43 level. As such, compositions comprising 2-(2,2,6,6-Tetramethylpiperidin-1-oxyl-4-ylamino)-2-oxoethyl)triphenylphosphonium chloride (MitoTEMPO) can be administered to individuals in need of reduced arrhythmic risk to increase connexin 43 level, thereby reducing or preventing arrhythmic risk.

While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

REFERENCES

The following references, including those cited in the disclosure herein, are hereby incorporated herein in their entirety by reference.

(1) Teo K K, Mitchell L B, Pogue J, Bosch J, Dagenais G, Yusuf S. Effect of ramipril in reducing sudden deaths and nonfatal cardiac arrests in high-risk individuals without heart failure or left ventricular dysfunction. *Circulation.* 2004; 110:1413-7.

(2) Kober L, Torp-Pedersen C, Carlsen J E, Bagger H, Eliasen P, Lyngborg K, Videbaek J, Cole D S, Auclert L, Pauly N C. A clinical trial of the angiotensin-converting-enzyme inhibitor trandolapril in patients with left ventricular dysfunction after myocardial infarction. Trandolapril Cardiac Evaluation (TRACE) Study Group. *N Engl J Med.* 1995; 333:1670-6.

(3) Xiao H D, Fuchs S, Campbell D J, Lewis W, Dudley S C, Jr., Kasi V S, Hoit B D, Keshelava G, Zhao H, Capecchi M R, Bernstein K E. Mice with cardiac-restricted angiotensin-converting enzyme (ACE) have atrial enlargement, cardiac arrhythmia, and sudden death. *Am J Pathol.* 2004; 165:1019-32.

(4) Sovari A A, Iravanian S, Dolmatova E, Jiao Z, Liu H, Zandieh S, kumar V, Wang K, Bernstein K E, Bonini M G, Duffy H S, Dudley S C. Inhibition of c-Src Tyrosine Kinase Prevents Angiotensin II-Mediated Connexin-43 Remodeling and Sudden Cardiac Death. *JACC.* 2011; 58:2332-9.

(5) Kasi V S, Xiao H D, Shang L L, Iravanian S, Langberg J, Witham E A, Jiao Z, Gallego C J, Bernstein K E, Dudley S C, Jr. Cardiac-restricted angiotensin-converting enzyme overexpression causes conduction defects and connexin dysregulation. *Am J Physiol Heart Circ Physiol.* 2007; 293:H182-H192.

(6) Iravanian S, Sovari A A, Lardin H A, Liu H, Xiao H D, Dolmatova E, Jiao Z, Harris B S, Witham E A, Gourdie R G, Duffy H S, Bernstein K E, Dudley S C, Jr. Inhibition of renin-angiotensin system (RAS) reduces ventricular tachycardia risk by altering connexin43. *J Mol Med* (Berl). 2011; 89:677-87.

(7) Morita N, Sovari A A, Xie Y, Fishbein M C, Mandel W J, Garfinkel A, Lin S F, Chen P S, Xie L H, Chen F, Qu Z, Weiss J N, Karagueuzian H S. Increased susceptibility of aged hearts to ventricular fibrillation during oxidative stress. *Am J Physiol Heart Circ Physiol.* 2009; 297: H1594-H1605.

(8) Sato D, Xie L H, Sovari A A, Tran D X, Morita N, Xie F, Karagueuzian H, Garfinkel A, Weiss J N, Qu Z. Synchronization of chaotic early afterdepolarizations in the genesis of cardiac arrhythmias. *Proc Natl Acad Sci USA.* 2009; 106:2983-8.

(9) Brown D A, O'Rourke B. Cardiac mitochondria and arrhythmias. *Cardiovasc Res.* 2010; 88:241-9.

(10) Jeong E M, Liu M, Sturdy M, Gao G, Varghese S T, Sovari A A, Dudley S C. Metabolic stress, reactive oxygen species, and arrhythmia. *J Mol Cell Cardiol.* 2012; 52:454-63.

(11) Sovari A A, Bonini M G, Dudley S C. Effective antioxidant therapy for the management of arrhythmia. *Expert Rev Cardiovasc Ther.* 2011; 9:797-800.

(12) Whaley-Connell A, Govindarajan G, Habibi J, Hayden M R, Cooper S A, Wei Y, Ma L, Qazi M, Link D, Karuparthi P R, Stump C, Ferrario C, Sowers J R. Angiotensin II-mediated oxidative stress promotes myocardial tissue remodeling in the transgenic (mRen2) 27 Ren2 rat. *Am J Physiol Endocrinol Metab.* 2007; 293:E355-E363.

(13) Sesso H D, Buring J E, Christen W G, Kurth T, Belanger C, MacFadyen J, Bubes V, Manson J E, Glynn R J, Gaziano J M. Vitamins E and C in the prevention of cardiovascular disease in men: the Physicians' Health Study II randomized controlled trial. *J Am Med Assoc.* 2008; 300:2123-33.

(14) Santos C X, Anilkumar N, Zhang M, Brewer A C, Shah A M. Redox signaling in cardiac myocytes. *Free Radic Biol Med.* 2011; 50:777-93.

(15) Stefanska J, Pawliczak R. Apocynin: molecular aptitudes. *Mediators Inflamm.* 2008; 2008:106507.

(16) de Mendez I, Garrett M C, Adams A G, Leto T L. Role of p67-phox SH3 domains in assembly of the NADPH oxidase system. *J Biol Chem.* 1994; 269:16326-32.

(17) Rees D D, Palmer R M, Schulz R, Hodson H F, Moncada S. Characterization of three inhibitors of endothelial nitric oxide synthase in vitro and in vivo. *Br J Pharmacol.* 1990; 101:746-52.

(18) Shen R S, Alam A, Zhang Y X. Inhibition of GTP cyclohydrolase I by pterins. *Biochim Biophys Acta.* 1988; 965:9-15.

(19) Pacher P, Nivorozhkin A, Szabo C. Therapeutic effects of xanthine oxidase inhibitors: renaissance half a century after the discovery of allopurinol. *Pharmacol Rev.* 2006; 58:87-114.

(20) Krishna M C, Grahame D A, Samuni A, Mitchell J B, Russo A. Oxoammonium cation intermediate in the nitroxide-catalyzed dismutation of superoxide. *Proc Natl Acad Sci USA.* 1992; 89:5537-41.

(21) Murphy M P, Smith R A. Targeting antioxidants to mitochondria by conjugation to lipophilic cations. *Annu Rev Pharmacol Toxicol.* 2007; 47:629-56.

(22) Liu M, Liu H, Dudley S C, Jr. Reactive oxygen species originating from mitochondria regulate the cardiac sodium channel. *Circ Res.* 2010; 107:967-74.

(23) Morita N, Lee J H, Xie Y, Sovari A, Qu Z, Weiss J N, Karagueuzian H S. Suppression of re-entrant and multifocal ventricular fibrillation by the late sodium current blocker ranolazine. *JACC.* 2011; 57:366-75.

(24) Morita N, Sovari A A, Xie Y, Fishbein M C, Mandel W J, Garfinkel A, Lin S F, Chen P S, Xie L H, Chen F, Qu Z, Weiss J N, Karagueuzian H S. Increased susceptibility of aged hearts to ventricular fibrillation during oxidative stress. *Am J Physiol Heart Circ Physiol.* 2009; 297: H1594-H1605.

(25) el-Fouly M H, Trosko J E, Chang C C. Scrape-loading and dye transfer. A rapid and simple technique to study gap junctional intercellular communication. *Exp Cell Res.* 1987; 168:422-30.

(26) Van Norstrand D W, Asimaki A, Rubinos C, Dolmatova E, Srinivas M, Tester D J, Saffitz J E, Duffy H S, Ackerman M J. Connexin43 mutation causes heterogeneous gap junction loss and sudden infant death. *Circulation.* 2011; 125:474-81.

(27) Roig E, Perez-Villa F, Morales M, Jimenez W, Orus J, Heras M, Sanz G. Clinical implications of increased plasma angiotensin II despite ACE inhibitor therapy in patients with congestive heart failure. *Eur Heart J.* 2000; 21:53-7.

(28) Gutstein D E, Morley G E, Tamaddon H, Vaidya D, Schneider M D, Chen J, Chien K R, Stuhlmann H, Fishman G I. Conduction slowing and sudden arrhythmic death in mice with cardiac-restricted inactivation of connexin43. *Circ Res.* 2001; 88:333-9.

(29) Reaume A G, de Sousa P A, Kulkarni S, Langille B L, Zhu D, Davies T C, Juneja S C, Kidder G M, Rossant J. Cardiac malformation in neonatal mice lacking connexin43. *Science.* 1995; 267:1831-4.

(30) Haendeler J, Hoffmann J, Brandes R P, Zeiher A M, Dimmeler S. Hydrogen peroxide triggers nuclear export of telomerase reverse transcriptase via Src kinase family-dependent phosphorylation of tyrosine 707. *Mol Cell Biol.* 2003; 23:4598-610.

(31) Aikawa R, Komuro I, Yamazaki T, Zou Y, Kudoh S, Tanaka M, Shiojima I, Hiroi Y, Yazaki Y. Oxidative stress activates extracellular signal-regulated kinases through Src and Ras in cultured cardiac myocytes of neonatal rats. *J Clin Invest.* 1997; 100:1813-21.

(32) Abadir P M, Foster D B, Crow M, Cooke C A, Rucker J J, Jain A, Smith B J, Burks T N, Cohn R D, Fedarko N S, Carey R M, O'Rourke B, Walston J D. Identification and characterization of a functional mitochondrial angiotensin system. *Proc Natl Acad Sci USA.* 2011; 108:14849-54.

(33) Ago T, Kuroda J, Pain J, Fu C, Li H, Sadoshima J. Upregulation of Nox4 by hypertrophic stimuli promotes apoptosis and mitochondrial dysfunction in cardiac myocytes. *Circ Res.* 2010; 106:1253-64.

(34) Kuroda J, Ago T, Matsushima S, Zhai P, Schneider M D, Sadoshima J. NADPH oxidase 4 (Nox4) is a major source of oxidative stress in the failing heart. *Proc Natl Acad Sci USA.* 2010; 107:15565-70.

(35) Bendall J K, Cave A C, Heymes C, Gall N, Shah A M. Pivotal role of a gp91(phox)-containing NADPH oxidase in angiotensin II-induced cardiac hypertrophy in mice. *Circulation.* 2002; 105:293-6.

(36) Doughan A K, Harrison D G, Dikalov S I. Molecular mechanisms of angiotensin II-mediated mitochondrial dysfunction: linking mitochondrial oxidative damage and vascular endothelial dysfunction. *Circ Res.* 2008; 102:488-96.

(37) Bedard K, Krause K H. The NOX family of ROS-generating NADPH oxidases: physiology and pathophysiology. *Physiol Rev.* 2007; 87:245-313.

(38) Dikalov S. Cross talk between mitochondria and NADPH oxidases. *Free Radic Biol Med.* 2011; 51:1289-301.

(39) Zorov D B, Juhaszova M, Sollott S J. Mitochondrial ROS-induced ROS release: an update and review. *Biochim Biophys Acta.* 2006; 1757:509-17.

(40) Beresewicz A, Horackova M. Alterations in electrical and contractile behavior of isolated cardiomyocytes by hydrogen peroxide: possible ionic mechanisms. *J Mol Cell Cardiol.* 1991; 23:899-918.

(41) Dikalova A E, Bikineyeva A T, Budzyn K, Nazarewicz R R, McCann L, Lewis W, Harrison D G, Dikalov S I. Therapeutic targeting of mitochondrial superoxide in hypertension. *Circ Res.* 2010; 107:106-16.

(42) Dai D F, Johnson S C, Villarin J J, Chin M T, Nieves-Cintron M, Chen T, Marcinek D J, Dorn G W, Kang Y J, Prolla T A, Santana L F, Rabinovitch P S. Mitochondrial oxidative stress mediates angiotensin II-induced cardiac hypertrophy and Gaq overexpression-induced heart failure. *Circ Res.* 2011; 108:837-46.

(43) van de Wal R M, Plokker H W, Lok D J, Boomsma F, van der Horst F A, van Veldhuisen D J, van Gilst W H, Voors A A. Determinants of increased angiotensin II levels in severe chronic heart failure patients despite ACE inhibition. *Int J Cardiol.* 2006; 106:367-72.

(44) Kober L, Torp-Pedersen C, Carlsen J E, Bagger H, Eliasen P, Lyngborg K, Videbaek J, Cole D S, Auclert L, Pauly N C. A clinical trial of the angiotensin-converting-enzyme inhibitor trandolapril in patients with left ventricular dysfunction after myocardial infarction. Trandolapril Cardiac Evaluation (TRACE) Study Group. *N Engl J Med.* 1995; 333:1670-6.

(45) Canton M, Menazza S, Sheeran F L, Polverino de LP, Di L F, Pepe S. Oxidation of myofibrillar proteins in human heart failure. *JACC.* 2011; 57:300-9.

(46) Banfi C, Brioschi M, Barcella S, Veglia F, Biglioli P, Tremoli E, Agostoni P. Oxidized proteins in plasma of patients with heart failure: role in endothelial damage. *Eur J Heart Fail.* 2008; 10:244-51.

(47) Bruce A F, Rothery S, Dupont E, Severs N J. Gap junction remodelling in human heart failure is associated with increased interaction of connexin43 with ZO-1. *Cardiovasc Res.* 2008; 77:757-65.

(48) Kaprielian R R, Gunning M, Dupont E, Sheppard M N, Rothery S M, Underwood R, Pennell D J, Fox K, Pepper J, Poole-Wilson P A, Severs N J. Downregulation of immunodetectable connexin43 and decreased gap junction size in the pathogenesis of chronic hibernation in the human left ventricle. *Circulation.* 1998; 97:651-60.

(49) Baines C P. How and when do myocytes die during ischemia and reperfusion: the late phase. *J Cardiovasc Pharmacol Ther.* 2011; 16:239-43.

(50) Kieken F, Mutsaers N, Dolmatova E, Virgil K, Wit A L, Kellezi A, Hirst-Jensen B J, Duffy H S, Sorgen P L. Structural and molecular mechanisms of gap junction remodeling in epicardial border zone myocytes following myocardial infarction. *Circ Res.* 2009; 104:1103-12.

What is claimed is:

1. In a cell having a reduced connexin 43 (Cx43) level associated with renin-angiotensin system (RAS) activation, a method of raising the Cx43 level to a normal level, comprising the step of exposing the cell to an effective amount of a mitochondria-targeted antioxidant thereby modulating connexin 43 (Cx43) level.

2. The method of claim 1, wherein the antioxidant comprises 2-(2,2,6,6-Tetramethylpiperidin-1-oxyl-4-ylamino)-2-oxoethyl)triphenylphosphonium chloride (MitoTEMPO).

3. The method of claim 1, wherein the cell comprises a cardiac cell.

4. A method of treating sudden cardiac death (SCD) associated with renin-angiotensin system (RAS) activation in a cell, comprising the step of administering a mitochondria-targeted antioxidant to a human or animal in need thereof to modulate connexin 43 (Cx43) level.

5. The method of claim 4, wherein the amount of the antioxidant is effective to reduce arrhythmic risk.

6. The method of claim 4, wherein the amount of the antioxidant is effective to restore the Cx43 to a normal level.

7. The method of claim 4, wherein the antioxidant restores the Cx43 level to a normal level by reducing or suppressing mitochondrial reactive oxidation species (ROS) production.

8. The method of claim 4, wherein the antioxidant comprises 2-(2,2,6,6-Tetramethylpiperidin-1-oxyl-4-ylamino)-2-oxoethyl)triphenylphosphonium chloride (MitoTEMPO).

9. The method of claim 8, wherein the amount of antioxidant is effective to result in a more than two-fold increase in the Cx43 level.

10. The method of claim 4, wherein the antioxidant is administered orally or intravenously.

11. The method of claim 4, wherein the human or animal is suffering from arrhythmia.

12. The method of claim 4, wherein the antioxidant comprises at least one member selected from the group consisting of a powder, a tablet, a capsule, a solution, a suspension, and an injectable formulation.

13. The method of claim 4, wherein the cell comprises a cardiac cell.

* * * * *